United States Patent

Schneider et al.

[11] Patent Number: 6,165,761
[45] Date of Patent: Dec. 26, 2000

[54] CARBOHYDRATE OXIDASE AND USE THEREOF IN BAKING

[75] Inventors: Palle Schneider, Ballerup; Søren Christensen, Copenhagen; Lone Dybdal, København; Claus Crone Fuglsang, Nivå, all of Denmark; Feng Xu, Woodland; Elizabeth Golightly, Davis, both of Calif.

[73] Assignee: Novo Nordisk A/S, Bagsvaerd, Denmark

[21] Appl. No.: 09/217,490

[22] Filed: Dec. 21, 1998

Related U.S. Application Data

[60] Provisional application No. 60/068,717, Dec. 23, 1997, and provisional application No. 60/088,725, Jun. 10, 1998.

[30] Foreign Application Priority Data

Dec. 22, 1997 [DK] Denmark ............................... 01505/97
Jun. 4, 1998 [DK] Denmark ............................ 1998 00763

[51] Int. Cl.[7] ............................... C12N 9/04; C12N 9/00
[52] U.S. Cl. .................. 435/190; 435/195; 435/197; 435/198; 435/200; 435/201; 435/202; 435/203; 435/204; 435/209
[58] Field of Search ..................... 435/190, 195, 435/200, 201, 202, 203, 204, 209, 198, 197

[56] References Cited

U.S. PATENT DOCUMENTS 2,783,150  2/1957  Luther ........................................ 99/93

FOREIGN PATENT DOCUMENTS 0321811   6/1989   European Pat. Off. .
0338452  10/1989   European Pat. Off. .
WO 96/39851 12/1996 WIPO .
WO 97/22257  6/1997 WIPO .

OTHER PUBLICATIONS

Shuen–Fuh Lin et al., (1993) Biotech. Advances 11:417–427.

Shuen–Fuh Lin et al., (1991) Biochemica et Biophysica Acta 1118:41–47.

*Primary Examiner*—Leon B. Lankford, Jr.
*Attorney, Agent, or Firm*—Elias J. Lambiris; Valeta Gregg

[57] ABSTRACT

The properties of dough or bread can be improved by the addition of a carbohydrate oxidase which can oxidize the reducing end of an oligosaccharide more efficiently than the corresponding monosaccharide, e.g., preferentially oxidizing maltodextrins or cellodextrins over glucose. A novel carbohydrate oxidase having the capability to oxidize maltodextrins and cellodextrins more efficiently than glucose may be obtained from a strain of Microdochium, particularly *M. nivale*. The amino acid sequence of the novel carbohydrate oxidase has very low homology (<20% identity) with known amino acid sequences.

13 Claims, 3 Drawing Sheets

Plasmid pBANe15

Plasmid pEJG33

Plasmid pEJG35 und 6,165,761

CARBOHYDRATE OXIDASE AND USE THEREOF IN BAKING

CROSS-REFERENCE TO RELATED APPLICATIONS

This application claims priority under 35 U.S.C. 119 of Danish applications PA 1997 01505 filed Dec. 22, 1997 and PA 1998 00763 filed Jun. 4, 1998, and of U.S. provisional application No. 60/068,717 filed Dec. 23, 1997 and provisional application No. 60/088,725 filed Jun. 10, 1998, the contents of which are fully incorporated herein by reference.

FIELD OF INVENTION

The present invention relates to the use in baking of a carbohydrate oxidase and to a novel carbohydrate oxidase.

DESCRIPTION OF THE RELATED ART

In the bread-making process it is known to add bread-improving and/or dough-improving additives to the bread dough, the action of which, inter alia, results in improved texture, volume, flavor and freshness of the bread as well as improved machinability and stability of the dough.

Dough "conditioners" to strengthen the gluten and improve the rheological and handling properties of the dough are well known in the industry and have long been used. Nonspecific oxidants, such as iodates, peroxides, ascorbic acid, potassium bromate and azodicarbonamide have a gluten strengthening effect. It has been suggested that these conditioners induce the formation of interprotein bonds which strengthen the gluten, and thereby the dough.

It is also known to use glucose oxidase to strengthen the gluten and improve the rheological and handling properties of the dough. Thus, U.S. Pat. No. 2,783,150 discloses the use of glucose oxidase in flour to improve dough strength, and texture and appearance of baked bread. EP 321 811 and EP 338 452 disclose the use in baking of glucose oxidase in combination with other enzymes (sulfhydryl oxidase, hemicellulase, cellulase). However, the effectiveness of glucose oxidase as a dough and/or bread improving additive is limited due to the generally low glucose content in cereal flours used in the preparation of baked products.

Thus there has been interest in identifying oxidoreductases which act on substrates other than glucose. WO 96/39851 discloses the use of a hexose oxidase which is capable of oxidizing D-glucose and several other reducing sugars including maltose, lactose, galactose, xylose, arabinose and cellobiose to their respective lactones with a subsequent hydrolysis to the respective aldobionic acids. WO 97/22257 discloses the use of a pyranose oxidase in baking. The enzyme catalyses the oxidation of several monosaccharides at position C2 with the concomitant release of hydrogen peroxide. Although glucose in its pyranose form tends to be the preferred substrate, the enzyme is capable of oxidizing other substrates, e.g., furanoses, such as xylose.

Although enzymes that catalyze the oxidation of glucose and other sugars directly to the corresponding aldonic acids appear to be widely distributed in nature, most of the known sugar oxidases are specific to monosaccharides. An oligosaccharide oxidase, isolated and purified from wheat bran culture of a soil-isolated *Acremonium strictum* strain T1, has been described by Lin, et al, (1991, Biochim. Biophys. Acta 1118:41–47). The enzyme has the capability of oxidizing oligosaccharides with a glucose residue on the reducing end. The enzyme demonstrated reactivity toward maltose, lactose, cellobiose and maltooligosaccharides composed of up to seven glucose units. JP-A 5-84074 discloses use of the enzyme as an analytical reagent.

SUMMARY OF THE INVENTION

The inventors have found that the properties of dough or bread can be improved by the addition of a carbohydrate oxidase which can oxidize the reducing end of an oligosaccharide more efficiently than the corresponding monosaccharide, e.g., preferentially oxidizing maltodextrins or cellodextrins over glucose. This can lead to improved firmness, stickiness, stability and robustness of the dough. It can also increase the tolerance of the dough towards increased mixing time, fermentation time and water content.

The inventors have also found a novel carbohydrate oxidase with the capability to oxidize maltodextrins and cellodextrins more efficiently than glucose. The novel oxidase may be obtained form Microdochium, particularly *M. nivale*. The inventors have isolated and deposited such a strain as *M. nivale* CBS 100236. The amino acid sequence of the novel carbohydrate oxidase has very low homology (<20% identity) with known amino acid sequences.

Accordingly, the invention provides a process for preparing a dough and/or a baked product made from a dough comprising adding to the dough a carbohydrate oxidase which has a higher activity on an oligosaccharide having a degree of polymerization of 2 or higher as a substrate than on the corresponding monosaccharide. The invention also provides a bread-improving additive comprising the carbohydrate oxidase. The bread-improving additive may comprise a second enzyme (amylase, cellulase, hemicellulase, lipase or phospholipase), and it may be in agglomerated powder or granulated form.

The invention further provides a novel carbohydrate oxidase. The carbohydrate oxidase may be a polypeptide produced by *Microdochium nivale* CBS 100236 or having an amino acid sequence as shown in SEQ ID NO: 2, or it may be an analogue thereof. The carbohydrate oxidase may also be derivable from a strain of Microdochium and have an oxidizing activity on maltotetraose which is at least twice as much as the oxidizing activity on glucose at a substrate concentration of 0.83 mM.

The invention also provides a method of producing said carbohydrate oxidase by cultivation of Microdochium. The invention further provides a nucleic aid construct comprising a nucleic acid sequence encoding the carbohydrate oxidase of the invention, recombinant expression vectors and recombinant host cells which are advantageously used in the recombinant production of the carbohydrate oxidase of the present invention. In yet a further aspect, the present invention provides recombinant methods for producing a carbohydrate oxidase of the invention comprising cultivating a host cell under conditions conducive to the production of the carbohydrate oxidase and recovering the carbohydrate oxidase from the cells and/or culture medium.

DETAILED DESCRIPTION OF THE INVENTION

Use of Carbohydrate Oxidase in Baking

Figure 1:
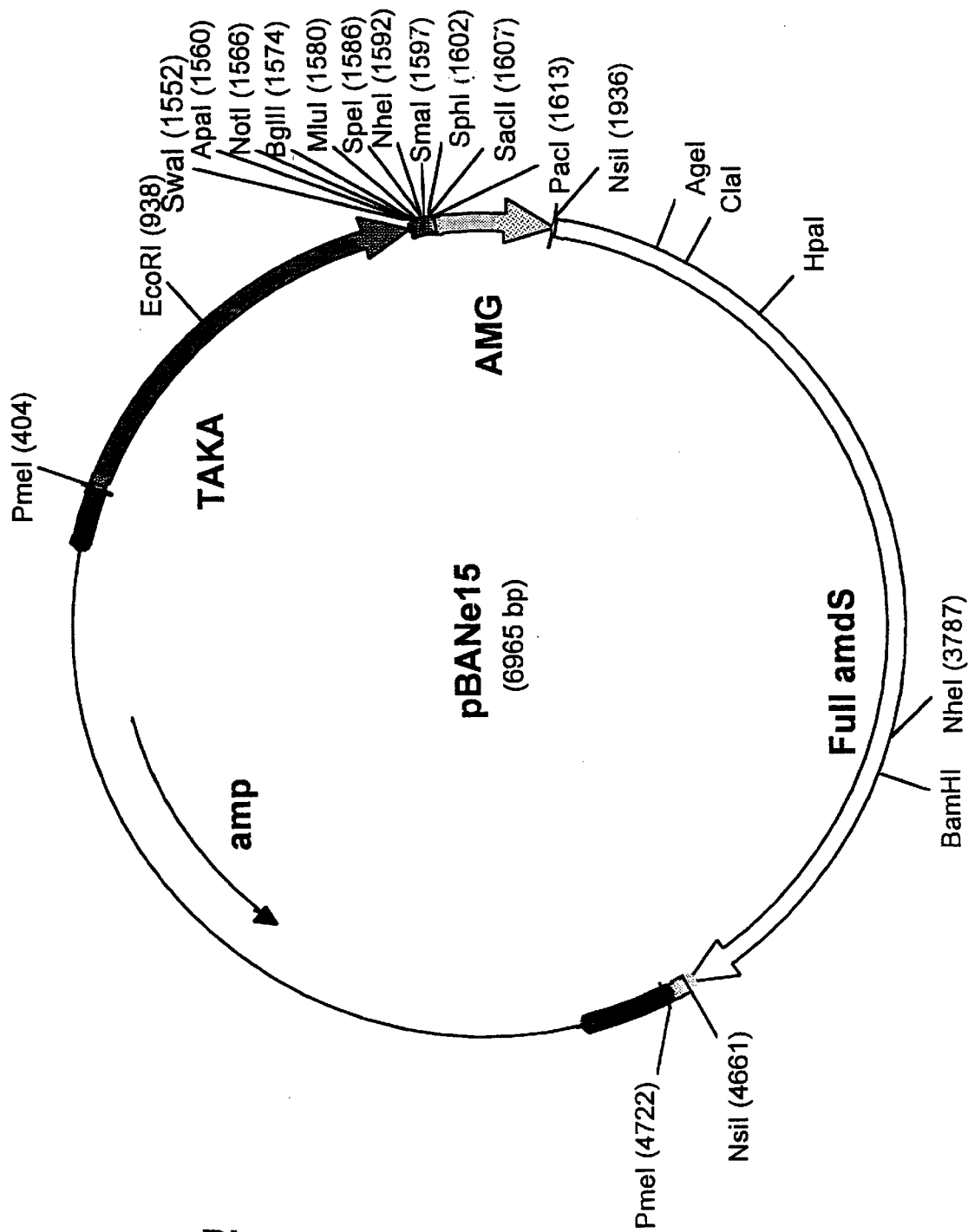
FIGS. 1–3 illustrate plasmids pBANe15, pEJG33 and pEJG35, respectively. Details are given in the Examples.
Figure 2:
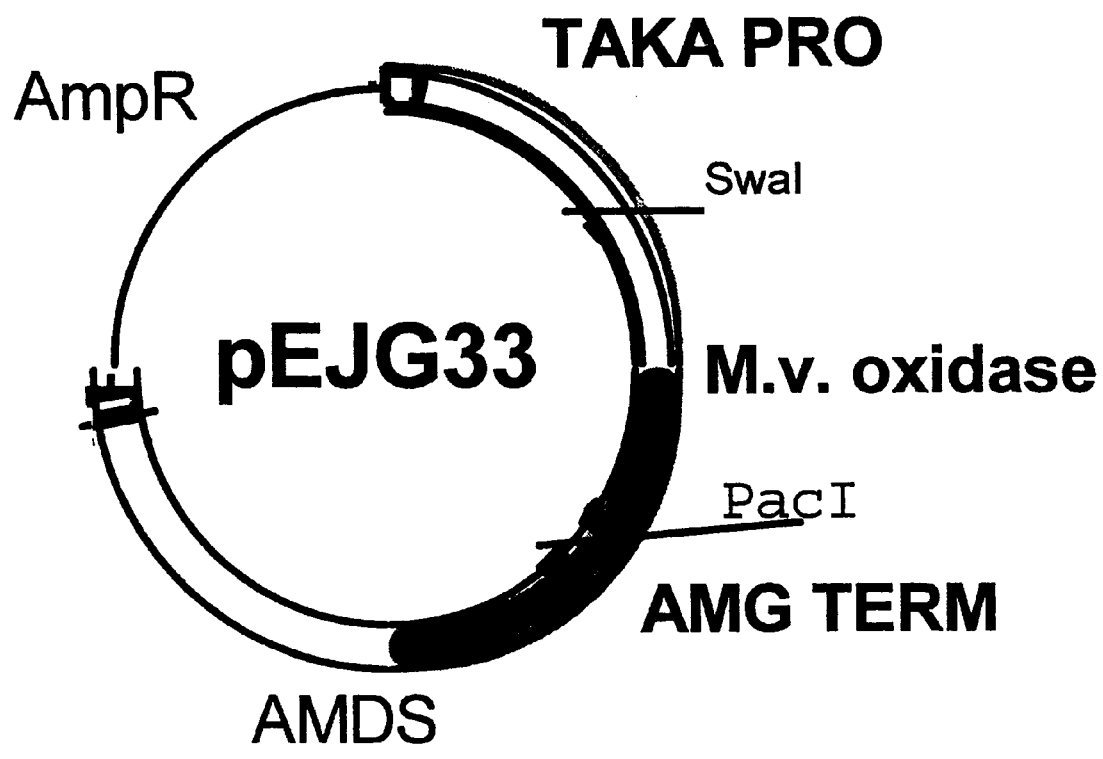
Figure 3:
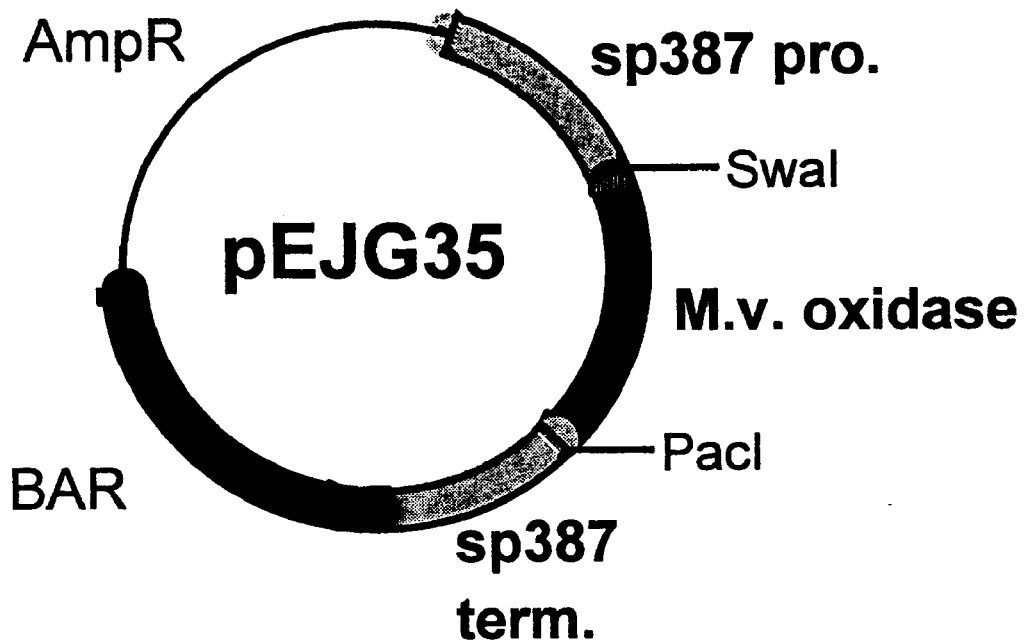

The present invention provides the addition to dough of a carbohydrate oxidase which has a higher activity on an oligosaccharide having a degree of polymerization of 2 or higher as a substrate than on the corresponding monosaccharide. The carbohydrate oxidase may be added in the form of a dough and/or bread-improving additive as described below.

The carbohydrate oxidase is generally added in amount which is effective for providing a measurable effect on at least one property of interest of the dough and/or baked product. The bread-improving and/or dough improving additive is generally included in the dough in an amount corresponding to 0.01–5%, in particular 0.1–3%. The enzyme is typically added in an amount corresponding to 0.01–100 mg enzyme protein per kg of flour, preferably 0.1–25 mg per kg, more preferably 0.1–10 mg per kg, and most preferably 0.5–5 mg per kg.

The level of oligosaccharides in dough can be increased by the addition of an amylase which hydrolyzes starch to form oligosaccharides as a main product, e.g., a Bacillus stearothermophilus maltogenic alpha-amylase (commercially available as Novamyl®), an Aspergillus oryzae alpha-amylase (commercially available as Fungamyl®) or a beta-amylase.

The use of an oligosaccharide oxidase may result in an increased volume and an improved crumb structure and softness of the baked product, as well as an increased strength, stability and reduced stickiness of the dough, thus resulting in improved machinability. The effect may be in addition to, or as a consequence of a gluten strengthening effect which is discussed below. The effect on the dough may be particularly advantageous when a poor quality flour is used. The improved machinability is of particular importance in connection with dough which is to be processed industrially.

Dough stability is one of the most important characteristics of a baking dough and is important for both large scale and small scale applications. A stable, or strong, dough is capable of a greater tolerance of mixing time, proofing time and of mechanical vibrations during dough transport, whereas a weak, or less stable, dough is less tolerant to these treatments. Whereas flour with a high gluten content and a good gluten quality contribute to a strong dough, flour containing a low protein content or with poor gluten quality results in a weak dough. Thus, a strong dough which has superior rheological and handling properties results from flour containing a strong gluten network.

The oligosaccharide oxidase may be added to any mixture of dough substances, to the dough, or to any of the substances to be included in the dough; that is, the oligosaccharide oxidase may be added in any step of the dough preparation and may be added in one, two or more steps, where appropriate and avoiding exposure of the enzyme to strong chemicals or conditions where it could become inactivated.

Substrate Specificity

The carbohydrate oxidase preferably has a higher activity on a maltooligosaccharide having a degree of polymerization of 2–6 (particularly maltose, maltotriose or maltotetraose) than on glucose at a substrate concentration of 10 mM or less. The comparison may be made at a substrate concentration of 1 mM or less, and the activity on maltotetraose is preferably more than twice of the activity on glucose. The carbohydrate oxidase may have an oxidizing activity on maltodextrins or cellodextrins maltotetraose which is at least two times the oxidizing activity on glucose at a substrate concentration of 0.83 mM.

Such substrate concentrations are representative of the concentration in typical doughs prepared according to usual baking practice. Thus, for example, in an extract made from a dough the concentration of maltose was found to be 4.1 mM, which corresponds to 41 mmoles/kg dough obtained from a 1:10 extraction for 1 hour at 40° C. as described by Poulsen, C., et al (1996. Cereal Chem., 75: 51–57). It was further mentioned that the amount of extractable maltose could be higher if sufficient endogenous amylolytic activity (e.g., beta-amylase) was present in the flour, or exogenous amylolytic enzymes was added to the dough or flour, as is often the practice. WO 96/39851 similarly discloses that maltose is present in dough at a level of 1.4% (w/w). Thus, the amount of available substrate, e.g., maltose, can differ depending on flour type and quality, recipe, mixing and fermentation process, as well as on the presence of other additives.

At pH 6 and 50 mM, a preferred carbohydrate oxidase from M. nivale has the following preference (descending order): cellobiose>maltose>glucose>xylose>lactose. Based on Michaeli-Menten kinetics, the apparent $K_m$ values for the preferred substrates are: 59 mM (cellobiose), 11 mM (maltose), 42 mM (glucose); $V_{max}$ is similar for glucose and maltose. Thus, the oxidase shows preference for maltose over glucose, particularly at low substrate concentrations (below 10 mM).

A preferred carbohydrate oxidase from M. nivale is capable of oxidizing oligosaccharides having a degree of polymerization (DP) of DP2-DP5, at a substrate concentration of 0.83 mM at a higher rate than the corresponding monosaccharide. Thus, the enzyme can hydrolyze both maltodextrins and cellodextrins wherein the monosaccharide units are linked by alpha-1,4 or beta-1,4 glucosidic bonds, respectively, at a higher rate than glucose. The carbohydrate oxidase can hydrolyze all cellodextrins having DP2-DP5 equally well and at a level around 10-fold higher than the monosaccharide glucose. With maltodextrins as the substrate, the activity of the carbohydrate oxidase ranged from 1½-fold higher for maltohexaose to almost 5-fold higher for maltotetraose than for the monosaccharide.

Carbohydrate Oxidase Properties

The carbohydrate oxidase is preferably active and stable at a pH in the range of 5–7, e.g. having more than 40% activity in this range, and most preferably having optimum activity in this range. A preferred carbohydrate oxidase from M. nivale has optimum activity around pH 6 and shows an activity which is at least 80% (relative to the maximum activity) in the pH range 5–7. At 40° C., it is stable in the pH range 4–9, but unstable at pH 3.

The carbohydrate oxidase is preferably active and stable at 20–45° C., e.g. having more than 50% activity in this range, and most preferably having optimum activity in this range. A preferred carbohydrate oxidase from M. nivale has optimum activity around 40° C. and exhibits at least 70% activity (relative to maximum activity) in the range 30–60° C. At pH 6, it is stable up to 60° C., but inactivated at 70° C. It has a denaturation temperature of 73° C.

The carbohydrate oxidase is able to oxidize reducing oligosaccharides with a glucose residue on the reducing end. It oxidizes the glucose residue at the 1-position to form the corresponding acid. Thus, it oxidizes maltose to form maltobionic acid and lactose to form lactobionic acid.

The carbohydrate oxidase activity may be isolated, e.g. essentially free of other non-carbohydrate oxidase polypeptides, for example, more than about 80% pure, and more preferably more than about 90% pure on a protein basis as determined by SDS-PAGE.

A preferred carbohydrate oxidase from M. nivale has a molecular weight of approximately 52 kDa as determined by SDS-PAGE and an isoelectric point of approximately 8.9. It shows dehydrogenase as a side activity with electron acceptors such as potassium ferricyanide, methylene blue, benzoquinone and 2,6-dichlorophenol-indophenol (DCPIP).

Sources of Carbohydrate Oxidase

The oligosaccharide oxidase may be obtained from a microbial source, such as a fungus, e.g., a filamentous fungus or a yeast, in particular an Ascomycota fungus, e.g. Euascomycetes, especially Pyrenomycetes.

The carbohydrate oxidase may be derived, e.g., from a mitosporic Pyrenomycetes such as Acremonium, in particular, *A. strictum*, such as ATCC 34717 or T1; *A. fusidioides*, such as IFO 6813; or *A. potronii*, such as IFO 31197. In a preferred embodiment, the oligosaccharide oxidase is obtained from the source disclosed by Lin, et al, (1991, Biochim. Biophys. Acta 1118:41–47) and in JP-A 5-84074.

The carbohydrate oxidase may further be obtained from microorganisms of Xylariales; especially mitosporic Xylariales such as the genus Microdochium, particularly the species *M. nivale*. Such strains are readily accessible to the public in culture collections, such as the American Type Culture Collection (ATCC), Deutsche Sammlung von Mikroorganismen und Zelikulturen GmbH (DSM) and Centraalbureau Voor Schimmelcultures (CBS).

The genus Microdochium is described in Microdochium Syd (Samuels and Hallett, 1983, TBMS 81:473). Some strains of Microdochium have been described under the synonyms Gerlachia, *G. nivalis, G. oryzae, Fusarium nivale* or *Rynchosporium oryzae*. They are further described by Monographella (Hyponectr) fide (Müller, 1977, Rev. mycol. 41:129).

A preferred strain is *M. nivale*, NN008551. This was isolated from natural sources taken in India and deposited according to the Budapest Treaty on the International Recognition of the Deposits of Microorganisms for the Purpose of Patent Procedures on Dec. 4, 1997 at the Centraalbureau voor Schimmelcultures under Accession No. CBS 100236.

The inventors have isolated the gene encoding the carbohydrate oxidase from *M. nivale* CBS 100236 and inserted it into *E. coli*. The *E. coli* strain harboring the gene was deposited according to the Budapest Treaty on the International Recognition of the Deposits of Microorganisms for the Purpose of Patent Procedures on Jun. 12, 1998 at the Agricultural Research Service Collection (NRRL), 1815 North University Street, Peoria, Ill., and designated NRRL B-30034.

Additional Enzyme

The carbohydrate oxidase may be added to the dough as the only enzyme, or it may be used in combination with one or more additional enzymes. The additional enzyme may be an amylase (e.g. as described above), a cyclodextrin glucanotransferase, a peptidase, in particular, an exopeptidase, a transglutaminase, a lipase, a phospholipase, a cellulase, a hemicellulase, in particular a pentosanase such as xylanase, a protease, a protein disulfide isomerase, e.g., a protein disulfide isomerase as disclosed in WO 95/00636, a glycosyltransferase, and an oxidoreduc-tase, e.g., a peroxidase, a laccase, a glucose oxidase, a pyranose oxidase, a lipoxygenase, an L-amino acid oxidase or an additional carbohydrate oxidase, and the like.

The additional enzyme may be of any origin, including mammalian and plant, and preferably of microbial (bacterial, yeast or fungal) origin and may be obtained by techniques conventionally used in the art.

The amylase may be derived from a bacterium or a fungus, in particular from a strain of Aspergillus, preferably a strain of *A. niger* or *A. oryzae*, or from a strain of Bacillus. Some examples are alpha-amylase, e.g. from *Bacillus amyloliquefaciens*, and amyloglucosidase, e.g. from *A. niger*. Commercial products include BAN and AMG (products of Novo Nordisk A/S, Denmark), Grindamyl A 1000 or A 5000 (available from Grindsted Products, Denmark) and Amylase H and Amylase P (products of Gist-Brocades, The Netherlands).

The protease may be Neutrase (available from Novo Nordisk A/S, Denmark).

The lipase may be derived from a strain of Thermomyces (Humicola), Rhizomucor, Candida, Aspergillus, Rhizopus, or Pseudomonas, in particular from *T. lanuginosus* (*H. lanuginosa*, EP 305,216), *Rhizomucor miehei* (EP 238,023), *C. antarctica* (e.g. Lipase A or Lipase B described in WO 88/02775), *A. niger, Rhizopus delemar* or *Rhizopus arrhizus* or *P. cepacia* (EP 214,761 and WO 89/01032).

Dough

The dough is generally a flour dough comprising wheat meal or wheat flour and/or other types of meal, flour or starch such as corn flour, corn starch, rye meal, rye flour, oat flour, oat meal, soy flour, sorghum meal, sorghum flour, rice starch, rice flour, potato meal, potato flour or potato starch.

The dough may be fresh, frozen or par-baked.

The dough is normally a leavened dough or a dough to be subjected to leavening. The dough may be leavened in various ways, such as by adding chemical leavening agents, e.g., sodium bicarbonate or by adding a leaven (fermenting dough), but it is preferred to leaven the dough by adding a suitable yeast culture, such as a culture of *Saccharomyces cerevisiae* (baker's yeast), e.g. a commercially available strain of *S. cerevisiae*.

The dough may also comprise other conventional dough ingredients, e.g.: proteins, such as milk or milk powder, gluten, and soy; eggs (either whole eggs, egg yolks or egg whites); shortening such as granulated fat or oil; an oxidant such as ascorbic acid, potassium bromate, potassium iodate, azodicarbonamide (ADA) or ammonium persulfate; a reducing agent such as L-cysteine; a sugar; a salt such as sodium chloride, calcium acetate, sodium sulfate or calcium sulfate. The dough may further comprise an emulsifier such as mono- or diglycerides, diacetyl tartaric acid esters of mono- or diglycerides, sugar esters of fatty acids, polyglycerol esters of fatty acids, lactic acid esters of monoglycerides, acetic acid esters of monoglycerides, polyoxyethylene stearates, phospholipids, lecithin and lysolecithin.

The dough may be a pasta dough, preferably prepared from durum flour or a flour of comparable quality. When used in the preparation of pasta and noodles, the carbohydrate oxidase may result in a strengthening of the gluten structure and thereby providing a reduction in stickiness of the dough, an increase in dough strength and a dough product with an improved texture.

Baked Product

The process of the invention may be used for any kind of baked product prepared from dough, either of a soft or a crisp character, either of a white, light or dark type. Examples are bread (in particular white, whole-meal or rye bread), typically in the form of loaves or rolls, French baguette-type bread, pita bread, tortillas, cakes, pancakes, biscuits, cookies, muffins, pie crusts, crisp bread, steamed bread, pizza and the like.

Pre-mix

The present invention further relates to a pre-mix, e.g., in the form of a flour composition, of dough and/or baked products made from dough, in which the pre-mix comprises the carbohydrate oxidase and optionally other enzymes as specified above. The pre-mix may be prepared by mixing enzyme the relevant enzyme(s) with a suitable carrier, such as flour, starch, a sugar or a salt. The pre-mix may contain other dough-improving and/or bread-improving additives, e.g. any of the additives, including enzymes, mentioned above.

Dough and/or Bread-improving Additive

The carbohydrate oxidase may be provided as a dough and/or bread improving additive in the form of a granulate or agglomerated powder. The dough and/or bread improving additive preferably has a narrow particle size distribution with more than 95% (by weight) of the particles in the range from 25 to 500 μm.

Granulates and agglomerated powders may be prepared by conventional methods, e.g. by spraying the amylase onto a carrier in a fluid-bed granulator. The carrier may consist of particulate cores having a suitable particle size. The carrier may be soluble or insoluble, e.g. a salt (such as NaCl or sodium sulfate), a sugar (such as sucrose or lactose), a sugar alcohol (such as sorbitol), starch, rice, corn grits, or soy.

Amino Acid Sequences

The carbohydrate oxidase may be a polypeptide which is produced by *Microdochium nivale* CBS 100236, has an amino acid sequence as shown in SEQ ID NO: 2, or is encoded by a gene present in *E. coli* NRRL B-30034; or it may be an analogue thereof. The analogue may have at least 50% identity, cross-react immunologically, be an allelic variant or a fragment having oxidase activity. The carbohydrate oxidase may further be a polypeptide encoded by a nucleic acid sequence which hybridizes under low stringency conditions with the nucleic acid sequence of SEQ ID NO:1, its complementary strand, or a subsequence thereof of at least 100 nucleotides.

The amino acid sequence shown in SEQ ID NO: 2 has less than 20% identity to known sequences. It is 13.6% identical to the amino acid sequence of a reticuline oxidase precursor from California poppy (GenPept Accession No. 2897944) and 17.8% identical to the amino acid sequence of a 6-hydroxy-D-nicotine oxidase from *Arthrobacter oxidans* (GenPept Accession No.122805).

An amino acid sequence of a polypeptide may be determined using standard methods for obtaining and sequencing peptides, for example as described by Findlay and Geisow, Eds., Protein Sequencing—a Practical Approach, 1989, IRL Press. A comparison with prior art amino acid sequences has shown that SEQ ID NO: 2 has only little homology (<20%) to any prior art amino acid sequence.

The polypeptide may be a variant having an amino acid sequence which differs by no more than three amino acids, preferably by no more than two amino acids, and more preferably by no more than one amino acid.

The carbohydrate oxidase may comprise at least one partial sequence which is the N-terminal amino acid sequence shown at positions 1–24 of SEQ ID NO: 2 or the internal sequences shown at positions 229–266, 249–271, 303–322, 336–347, 383–404, 405–414 and 420–440 of SEQ ID NO: 2. Alternatively, the carbohydrate oxidase may be at least 50% identical with at least one of said partial sequences, preferably at least 60%, more preferably at least 70%, even more preferably at least 80%, even more preferably at least 90%, and most preferably at least 97%, which qualitatively retain the activity of the carbohydrate oxidase (hereinafter referred to as "homologous carbohydrate oxidase") and allelic forms and fragments thereof, wherein the fragments retain carbohydrate oxidase activity.

In a preferred embodiment, the homologous carbohydrate oxidase comprises an amino acid sequence which differs by five amino acids, preferably by four amino acids, more preferably by three amino acids, even more preferably by two amino acids, and most preferably by one amino acid from at least one of said partial amino acid sequences. The carbohydrate oxidase may comprise an allelic form or fragment thereof, wherein the fragment retains carbohydrate oxidase activity.

The amino acid sequence of the homologous carbohydrate oxidase may differ from any of the partial amino acid sequences by an insertion or deletion of one or more amino acid residues and/or the substitution of one or more amino acid residues by different amino acid residues. The amino acid changes are preferably of a minor nature, that is, conservative amino acid substitutions that do not significantly affect the tertiary structure and/or activity of the carbohydrate oxidase. Minor amino acid changes may also include small deletions, typically of one to about 30 amino acids; small amino- or carboxyl-terminal extensions, such as an amino-terminal methionine residue; a small linker peptide of up to about 20–25 residues; or a small extension that facilitates purification by changing net charge or another function, such as a polyhistidine tract, an antigenic epitope or a binding domain.

Examples of conservative substitutions are within the group of basic amino acids (such as arginine, lysine and histidine), acidic amino acids (such as glutamic acid and aspartic acid), polar amino acids (such as glutamine and asparagine), hydrophobic amino acids (such as leucine, isoleucine and valine), aromatic amino acids (such as phenylalanine, tryptophan and tyrosine) and small amino acids (such as glycine, alanine, serine, and threonine). Amino acid substitutions which do not generally alter the specific activity are known in the art and are described, e.g., by H. Neurath and R. L. Hill, 1979, in The Proteins, Academic Press, New York. The most commonly occurring exchanges are: Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, Asp/Gly as well as these in reverse.

Nucleic Acid Sequences

The invention provides a nucleic acid sequence comprising a nucleic acid sequence which encodes the carbohydrate oxidase. The carbohydrate oxidase-encoding nucleic acid sequence may comprise:

a) the carbohydrate oxidase encoding part of the DNA sequence cloned into a plasmid present in *Escherichia coli* NRRL B-30034, or b) the DNA sequence shown in positions 67–1550 of SEQ ID NO: 1, or c) an analogue of the DNA sequence defined in a) or b) which
   i) has at least 50% identity with said DNA sequence, or
   ii) hybridizes at low stringency with said DNA sequence, its complementary strand or a subsequence thereof.

The degree of identity may be at least 60%, preferably about 70%, preferably about 80%, more preferably about 90%, even more preferably about 95%, and most preferably about 97%.

An allelic variant denotes any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Hybridization indicates that the analogous nucleic acid sequence hybridizes to the oligonucleotide probe under low, medium or high stringency conditions (for example, prehybridization and hybridization at 42° C. in 5×SSPE, 0.3% SDS, 200 mg/ml sheared and denatured salmon sperm DNA, and either 50, 35 or 25% formamide for high, medium and low stringencies, respectively), following standard Southern blotting procedures. In a preferred embodiment, the nucleic acid sequences are capable of hybridizing under high stringency conditions with the carbohydrate oxidase encoding region of at the nucleic acid sequence for the carbohydrate oxidase of the present invention harbored in CBS 100236, its complementary strand, or a subsequence thereof.

The DNA sequence encoding a carbohydrate oxidase may be isolated from any cell or microorganism producing the carbohydrate oxidase in question, using various methods well known in the art to relocate the nucleic acid sequence from its natural location to a different site where it will be reproduced.

The carbohydrate oxidase encoding region of the nucleic acid sequence harbored in CBS 100236, or subsequences thereof, may be used to design an oligonucleotide probe to isolate homologous genes encoding carbohydrate oxidases from other strains of different genera or species according to methods well known in the art. Thus, a genomic or cDNA library prepared from such other organisms may be screened for DNA which hybridizes with such probes following standard Southern blotting procedures, in order to identify and isolate the corresponding gene therein. Such probes can be considerably shorter than the entire sequence, but should be at least 15, preferably at least 25, and more preferably at least 40 nucleotides in length. Longer probes, preferably no more than 1200 nucleotides in length, can also be used. Both DNA and RNA probes can be used. The probes are typically labeled for detecting the corresponding gene (for example, with 32P, 3H, biotin, or avidin). According to the present invention, preferred probes may be constructed on the basis of SEQ ID NO: 1.

Genomic or other DNA from such other organisms may be separated by agarose or polyacrylamide gel electrophoresis, or other separation techniques known in the art. DNA from the libraries or the separated DNA may be transferred to and immobilized on nitrocellulose or other suitable carrier material. In order to identify clones or DNA which are homologous with the nucleic acid sequence for the carbohydrate oxidase of the present invention harbored in CBS 100236, the carrier material is used in a Southern blot in which the carrier material is finally washed three times for 30 minutes each using 2×SSC, 0.2% SDS at preferably not higher than 40° C., more preferably not higher than 45° C., more preferably not higher than 50° C., more preferably not higher than 55° C., even more preferably not higher than 60° C., especially not higher than 65° C. Molecules to which the oligonucleotide probe hybridizes under these conditions are detected using X-ray film.

The isolated nucleic acid sequences of the present invention which are capable of hybridizing with an oligonucleotide probe which hybridizes with the nucleic acid sequence for the carbohydrate oxidase of the present invention harbored in CBS 100236, its complementary strand, or a subsequence thereof, may be obtained from microorganisms of any genus, for example, from a bacterial or fungal source.

The carbohydrate oxidase may be obtained from (or endogenous to) a given microbial source. Thus, the carbohydrate oxidase may be produced by the source organism or by a cell in which a gene from the source has been inserted.

Furthermore, homologous genes may be identified and obtained from other sources including microorganisms isolated from nature (e.g., soil, composts, water, etc.) using the above-mentioned probes. Techniques for isolating microorganisms from natural habitats are well known in the art. The nucleic acid sequence may then be derived by similarly screening a genomic or cDNA library of another microorganism.

Once a nucleic acid sequence has been detected with the probe(s) described above, the sequence may be isolated or cloned by utilizing techniques which are well known to those of ordinary skill in the art (see, e.g., Sambrook et al., 1989, supra). The known techniques used to isolate or clone a nucleic acid sequence include isolation from genomic DNA, preparation from cDNA, or a combination thereof. The cloning of the nucleic acid sequences of the present invention from such genomic DNA can be effected, e.g., by using the well known polymerase chain reaction (PCR) using specific primers, for instance as described in U.S. Pat. No. 4,683,202 or R. K. Saiki et al. (1988, Science 239:487–491). Also see, for example, Innis, et al., 1990, PCR Protocols: A Guide to Methods and Application, Academic Press, New York. The nucleic acid sequence may be cloned from an organism producing the carbohydrate oxidase, or another or related organism and thus, for example, may be an allelic or species variant of the carbohydrate oxidase encoding region of the nucleic acid sequence.

Alternatively, the DNA sequence encoding the enzyme may be prepared synthetically by established standard methods, e.g. the phosphoamidite method described by S. L. Beaucage and M. H. Caruthers (1981, Tetrahedron Letters 22:1859–1869) or the method described by Matthes et al. (1984, The EMBO J. 3:801–805). In the aforementioned phosphoamidite method, oligonucleotides are synthesized, e.g. in an automatic DNA synthesizer, purified, annealed, ligated and cloned in appropriate vectors.

Modification of the nucleic acid sequence encoding the carbohydrate oxidase may be necessary for the synthesis of a carbohydrate oxidase substantially similar to the carbohydrate oxidase. The term "substantially similar" to the carbohydrate oxidase refers to non-naturally occurring forms of the carbohydrate oxidase. This carbohydrate oxidase may differ in some engineered way from the carbohydrate oxidase isolated from its native source. For example, it may be of interest to synthesize variants of the carbohydrate oxidase where the variants differ in specific activity, thermostability, oxidative stability, pH optimum, or the like using, for example, site-directed mutagenesis. The analogous sequence may be constructed on the basis of the carbohydrate oxidase encoding region of the nucleic acid sequence for the carbohydrate oxidase of the present invention harbored in CBS 100236, a subsequence thereof, and/or by introduction of nucleotide substitutions which do not give rise to another amino acid sequence of the carbohydrate oxidase encoded by the nucleic acid sequence, but which corresponds to the codon usage of the host organism intended for production of the enzyme, or by introduction of nucleotide substitutions which may give rise to a different amino acid sequence. For a general description of nucleotide substitution, see, e.g., Ford, et al., 1991, Protein Expression and Purification 2:95–107.

Such substitutions can be made outside the regions critical to the function of the molecule and still result in an active carbohydrate oxidase. Amino acid residues essential to the activity of the carbohydrate oxidase encoded by the isolated nucleic acid sequence, and therefore preferably not subject to substitution, may be identified according to procedures known in the art, such as site-directed mutagenesis or alanine-scanning mutagenesis (see, e.g., Cunningham and Wells, 1989, Science 244:1081–1085). In the latter technique, mutations are introduced at every positively charged residue in the molecule, and the resultant mutant molecules are tested for protease activity to identify amino acid residues that are critical to the activity of the molecule. Sites of substrate-enzyme interaction can also be determined by analysis of crystal structure as determined by such techniques as nuclear magnetic resonance analysis, crystallography or photoaffinity labeling (see, e.g., de Vos et al., 1992, Science 255:306–312; Smith, et al., 1992, Journal of Molecular Biology 224:899–904; Wlodaver, et al., 1992, FEBS Letters 309:59–64).

The carbohydrate oxidase may be a fused polypeptide in which another polypeptide is fused at the N-terminus or the C-terminus of the polypeptide or fragment thereof. A fused polypeptide is produced by fusing a nucleic acid sequence (or a portion thereof) encoding another polypeptide to a nucleic acid sequence (or a portion thereof) of the present invention. Techniques for producing fusion polypeptides are known in the art, and include, ligating the coding sequences encoding the polypeptides so that they are in frame and that expression of the fused polypeptide is under control of the same promoter(s) and terminator.

Yet another method for identifying carbohydrate oxidase-encoding clones would involve inserting fragments of genomic DNA into an expression vector, such as a plasmid, transforming carbohydrate oxidase-negative bacteria with the resulting genomic DNA library, and then plating the transformed bacteria onto agar containing a substrate for carbohydrate oxidase, thereby allowing clones expressing carbohydrate oxidase to be identified.

Finally, the DNA sequence may be of mixed genomic and synthetic origin, mixed synthetic and cDNA origin or mixed genomic and cDNA origin, prepared in accordance with standard techniques by ligating fragments of synthetic, genomic or cDNA origin as appropriate wherein the fragments correspond to various sections of the entire DNA sequence.

Identity of Amino Acid or Nucleic Acid Sequences

The polypeptide identity referred to in this specification with claims is determined as the degree of identity between two sequences indicating a derivation of the first sequence from the second. The identity may suitably be determined according to the method described in Needleman, S. B. and Wunsch, C. D., (1970), Journal of Molecular Biology, 48, 443–45, with the following settings for polypeptide sequence comparison: GAP creation penalty of 3.0 and GAP extension penalty of 0.1. The determination may be done by means of a computer program known such as GAP provided in the GCG program package (Program Manual for the Wisconsin Package, Version August 8, 1994, Genetics Computer Group, 575 Science Drive, Madison, Wis., USA 53711).

Alternatively, the degree of identity may be determined by the Clustal method (Higgins, 1989, *CABIOS* 5: 151–153) using the LASERGENE™ MEGALIGN™ software (DNASTAR, Inc., Madison, Wis.) with an identity table and the following multiple alignment parameters: Gap penalty of 10, and gap length penalty of 10. Pairwise alignment parameters were Ktuple=1, gap penalty=3, windows=5, and diagonals=5.

The mature region of an analogous polypeptide may exhibit a degree of identity preferably of at least 60%, more preferably at least 70%, more preferably at least 80%, more preferably at least 90%, and especially at least 95% with the sequence of the carbohydrate oxidase described above.

For purposes of the present invention, the degree of identity between two nucleic acid sequences is determined by the Clustal method (Higgins, 1989, *CABIOS* 5: 151–153) with an identity table, a gap penalty of 10, and a gap length penalty of 10.

Immunochemical Properties

The carbohydrate oxidase may have immunochemical identity or partial immunochemical identity to a carbohydrate oxidase native to a strain of *M. nivale*, or a teleomorph thereof, expressing carbohydrate oxidase activity. In this embodiment, said carbohydrate oxidase is used to produce antibodies which are immunoreactive or bind to epitopes of the polypeptide.

A polypeptide has immunochemical identity to the polypeptide native to *M. nivale* means if an antiserum containing antibodies against the polypeptide native to *M. nivale* reacts with the other polypeptide in an identical manner, such as total fusion of precipitates, identical precipitate morphology, and/or identical electrophoretic mobility using a specific immunochemical technique. A further explanation of immunochemical identity is described by Axelsen, Bock, and Krøll in N. H. Axelsen, J. Krøll, and B. Weeks, editors, A Manual of Quantitative Immunoelectrophoresis, Blackwell Scientific Publications, 1973, Chapter 10.

Partial immunochemical identity means that an antiserum containing antibodies against the polypeptide native to *M. nivale* reacts with the other polypeptide in a partially identical manner, such as partial fusion of precipitates, partially identical precipitate morphology, and/or partially identical electrophoretic mobility using a specific immunochemical technique. A further explanation of partial immunochemical identity is described by Bock and Axelsen in N. H. Axelsen, J. Krøll, and B. Weeks, editors, A Manual of Quantitative Immunoelectrophoresis, Blackwell Scientific Publications, 1973, Chapter 11.

The immunochemical properties may be determined by immunological cross-reaction identity tests, such as the well-known Ouchterlony double immunodiffusion procedure. Specifically, an antiserum against the polypeptide is raised by immunizing rabbits (or rodents) according to the procedure described by Harboe and Ingild, in A Manual of Quantitative Immunoelectrophoresis, N. H. Axelsen, J. Krøll, and B. Weeks, editors, Blackwell Scientific Publications, 1973, Chapter 23, or Johnstone and Thorpe in Immunochemistry in Practice, Blackwell Scientific Publications, 1982 (more specifically pages 27–31).

Preferably, the antibodies are monoclonal antibodies. Monoclonal antibodies may be prepared, e.g., according to the methods described in Antibodies, A Laboratory Manual, E. Harlow and D. Lane, editors, 1988, Cold Spring Harbor Press, Cold Spring Harbor, N.Y. Purified immunoglobulins may be obtained from the antiserum, e.g., by ammonium sulfate precipitation, followed by dialysis and ion exchange chromatography (e.g., DEAE-Sephadex).

Production of Carbohydrate Oxidase

The carbohydrate oxidase may be produced by fermentation of the above mentioned microbial strain on a nutrient medium containing suitable carbon and nitrogen sources and inorganic salts, using procedures known in the art (e.g., Bennett, J. W., and La Sure, L., eds., More Gene Manipulations in Fungi, Academic Press, CA, 1991.) Suitable media are available from commercial suppliers or may be prepared according to published compositions (e.g., in catalogues of the American Type Culture Collection). A temperature in the range of from 20° C. to 30° C. is suitable for growth and carbohydrate oxidase production.

The fermentation may be any method of cultivation of a cell resulting in the expression or isolation of said carbohydrate oxidase. Fermentation may therefore be understood as comprising shake flask cultivation, small or large scale fermentation (including continuous, batch, fed-batch, or solid state fermentations) in laboratory or industrial fermentors performed in a suitable medium and under conditions allowing the carbohydrate oxidase to be expressed or isolated.

The resulting carbohydrate oxidase produced by the methods described above may be recovered from the fermentation medium by conventional procedures including, but not limited to, centrifugation, filtration, spray-drying, evaporation, or precipitation. The recovered protein may then be further purified by a variety of chromatographic procedures, e.g., ion exchange chromatography, gel filtration chromatography, affinity chromatography, or the like.

The carbohydrate oxidase may be produced by a method comprising (a) cultivating an organism, which in its wild-type form expresses the carbohydrate oxidase, to produce a supernatant comprising the carbohydrate oxidase; and (b) recovering the carbohydrate oxidase.

Alternatively, the carbohydrate oxidase may be produced by aerobic cultivation of a transformed host organism containing the appropriate genetic information from the above mentioned strain. Such transformants can be prepared and cultivated by methods known in the art as described below.

Nucleic Acid Constructs

The present invention also relates to nucleic acid constructs comprising a nucleic acid sequence of the present invention operably linked to one or more control sequences capable of directing the expression of the coding sequence in a suitable host cell under conditions compatible with the control sequences.

The nucleic acid construct may be a nucleic acid molecule, either single- or double-stranded, which is isolated from a naturally occurring gene or which has been modified to contain segments of nucleic acid which are combined and juxtaposed in a manner which would not otherwise exist in nature. The nucleic acid construct may be an expression cassette when the nucleic acid construct contains all the control sequences required for expression of a coding sequence of the present invention. The coding sequence may be a sequence which is transcribed into mRNA and translated into a carbohydrate oxidase of the present invention when placed under the control of the appropriate control sequences. The boundaries of the coding sequence are generally determined by a translation start codon ATG at the 5'-terminus and a translation stop codon at the 3'-terminus. A coding sequence can include, but is not limited to, DNA, cDNA, and recombinant nucleic acid sequences.

An isolated nucleic acid sequence of the present invention may be manipulated in a variety of ways to provide for expression of the carbohydrate oxidase. Manipulation of the nucleic acid sequence prior to its insertion into a vector may be desirable or necessary depending on the expression vector. The techniques for modifying nucleic acid sequences utilizing cloning methods are well known in the art.

The control sequences may include all components which are necessary or advantageous for expression of the coding sequence of the nucleic acid sequence. Each control sequence may be native or foreign to the nucleic acid sequence encoding the carbohydrate oxidase. Such control sequences include, but are not limited to, a leader, a promoter, a signal sequence, and a transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleic acid sequence encoding a carbohydrate oxidase.

The control sequence may be an appropriate promoter sequence, a nucleic acid sequence which is recognized by the host cell for expression of the nucleic acid sequence. The promoter sequence contains transcription control sequences which mediate the expression of the carbohydrate oxidase. The promoter may be any nucleic acid sequence which shows transcriptional activity in the host cell of choice and may be obtained from genes encoding extracellular or intracellular carbohydrate oxidase either homologous or heterologous to the host cell.

Examples of suitable promoters for directing the transcription of the nucleic acid constructs of the present invention, especially in a bacterial host, are the promoters obtained from the *E. coli* lac operon, the *Streptomyces coelicolor* agarase gene (dagA), the *Bacillus subtilis* levansucrase gene (sacB), the *Bacillus licheniformis* alpha-amylase gene (amyL), the *Bacillus stearothermophilus* maltogenic amylase gene (amyM), the *Bacillus amyloliquefaciens* alpha-amylase gene (amyQ), the *Bacillus licheniformis* penicillinase gene (penP), the *Bacillus subtilis* xylA and xylB genes, and the prokaryotic beta-lactamase gene (Villa-Kamaroff et al., 1978, Proceedings of the National Academy of Sciences USA 75: 3727–3731), as well as the tac promoter i (DeBoer et al., 1983, Proceedings of the National Academy of Sciences USA 80: 21–25). Further promoters are described in "Useful proteins from recombinant bacteria" in Scientific American, 1980, 242: 74–94; and in Sambrook et al., 1989, supra.

For transcription in a fungal host, examples of useful promoters include those derivable from the gene encoding the Aspergillus oryzae TAKA amylase, Rhizomucor miehei aspartic proteinase, *A. niger* neutral a-amylase, *A. niger* acid stable a-amylase, *A. niger* glucoamylase, Rhizomucor miehei lipase, *A. oryzae* alkaline protease, *A. oryzae* triose phosphate isomerase and *A. nidulans* acetamidase.

The control sequence may also be a suitable transcription terminator sequence, a sequence recognized by the host cell of choice to terminate transcription. The terminator sequence is operably linked to the 3' terminus of the nucleic acid sequence encoding the carbohydrate oxidase. Any terminator which is functional in the host cell of choice may be used in the present invention.

The control sequence may also be a suitable leader sequence, a nontranslated region of a mRNA which is important for translation by the host cell. The leader sequence is operably linked to the 5' terminus of the nucleic acid sequence encoding the carbohydrate oxidase. Any leader sequence which is functional in the host cell of choice may be used in the present invention.

The control sequence may also be a signal peptide coding region, which codes for an amino acid sequence linked to the amino terminus of the carbohydrate oxidase which can direct the expressed carbohydrate oxidase into the cell's secretory pathway. The signal peptide coding region may be native to the carbohydrate oxidase or may be obtained from foreign sources. The 5' end of the coding sequence of the nucleic acid sequence may inherently contain a signal peptide coding region naturally linked in translation reading frame with the segment of the coding region which encodes the secreted carbohydrate oxidase. Alternatively, the 5' end of the coding sequence may contain a signal peptide coding region which is foreign to that portion of the coding sequence which encodes the secreted carbohydrate oxidase. The foreign signal peptide coding region may be required where the coding sequence does not normally contain a signal peptide coding region. Alternatively, the foreign signal peptide coding region may simply replace the natural signal peptide coding region in order to obtain enhanced secretion of the carbohydrate oxidase relative to the natural signal peptide coding region normally associated with the coding sequence. Any signal peptide coding region capable of directing the expressed carbohydrate oxidase into the secretory pathway of the host cell of choice may be used in the present invention.

An effective signal peptide coding region for a bacterial host cell, in particular, Bacillus, is the signal peptide coding region obtained from the maltogenic amylase gene from Bacillus NCIB 11837, the *Bacillus stearothermophilus* alpha-amylase gene, the *Bacillus licheniformis* subtilisin gene, the *Bacillus licheniformis* beta-lactamase gene, the *Bacillus stearothermophilus* neutral proteases genes (nprT, nprS, nprM), and the *Bacillus subtilis* prsA gene. Further signal peptides are described by Simonen and Palva, 1993, Microbiological Reviews 57: 109–137.

Expression Vectors

The present invention also relates to recombinant expression vectors comprising a nucleic acid sequence of the present invention, a promoter, and transcriptional and translational stop signals. The various nucleic acid and control sequences described above may be joined together to produce a recombinant expression vector which may include one or more convenient restriction sites to allow for insertion or substitution of the nucleic acid sequence encoding the carbohydrate oxidase at such sites. Alternatively, the nucleic acid sequence of the present invention may be expressed by inserting the nucleic acid sequence or a nucleic acid construct comprising the sequence into an appropriate vector for expression. In creating the expression vector, the coding sequence is located in the vector so that the coding sequence is operably linked with the appropriate control sequences for expression, and possibly secretion.

The expression vector may also comprise in eukaryotes a poly-adenylation sequences operably linked to the DNA sequence encoding the carbohydrate oxidase. Termination and poly-adenylation sequences may be suitably derived from the same sources as the promoter.

The recombinant expression vector may be any vector which can be conveniently subjected to recombinant DNA procedures and can bring about the expression of the nucleic acid sequence. The choice of the vector will typically depend on the compatibility of the vector with the host cell into which the vector is to be introduced. The vectors may be linear or closed circular plasmids. The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. The vector system may be a single vector or plasmid, two or more vectors or plasmids which together contain the total DNA to be introduced into the genome of the host cell, or a transposon.

The vectors of the present invention preferably contain one or more selectable markers which permit easy selection of transformed cells. A selectable marker is a gene the product of which provides for biocide resistance, resistance to heavy metals, prototrophy to auxotrophs, and the like. Examples of bacterial selectable markers are the dal genes from *Bacillus subtilis* or *Bacillus licheniformis*, or markers which confer antibiotic resistance such as ampicillin, kanamycin, erythromycin, chloramphenicol or tetracycline resistance. Furthermore, selection may be accomplished by cotransformation, e.g., as described in WO 91/09129, where the selectable marker is on a separate vector.

The vectors of the present invention contain an element(s) that permits stable integration of the vector into the host cell genome or autonomous replication of the vector in the cell independent of the genome of the cell.

The vectors of the present invention may be integrated into the host cell genome when introduced into a host cell. For integration, the vector may rely on the nucleic acid sequence encoding the carbohydrate oxidase or any other element of the vector for stable integration of the vector into the genome by homologous recombination. Alternatively, the vector may contain additional nucleic acid sequences for directing integration by homologous recombination into the genome of the host cell. The additional nucleic acid sequences enable the vector to be integrated into the host cell genome at a precise location in the chromosome. To increase the likelihood of integration at a precise location, the integrational elements should preferably contain a sufficient number of nucleic acids, such as 100 to 1,500 base pairs, preferably 400 to 1,500 base pairs, and most preferably 800 to 1,500 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleic acid sequences.

For autonomous replication, the vector may further comprise an origin of replication enabling the vector to replicate autonomously in the host cell in question. Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in Bacillus. The origin of replication may be one having a mutation to make its function temperature-sensitive in the Bacillus cell (see, e.g., Ehrlich, 1978, Proceedings of the National Academy of Sciences USA 75:1433).

More than one copy of a nucleic acid sequence encoding a carbohydrate oxidase of the present invention may be inserted into the host cell to amplify expression of the nucleic acid sequence. Stable amplification of the nucleic acid sequence can be obtained by integrating at least one additional copy of the sequence into the host cell genome using methods well known in the art and selecting for transformants. A convenient method for achieving amplification of genomic DNA sequences is described in WO 94/14968.

Procedures suitable for constructing vectors encoding a carbohydrate oxidase and containing the promoter, terminator and other elements, respectively, are well known to persons skilled in the art (c.f., for instance, Sambrook et al., supra).

It may also be desirable to add regulatory sequences which allow the regulation of the expression of the carbohydrate oxidase relative to the growth of the host cell. Examples of regulatory systems are those which cause the expression of the gene to be turned on or off in response to a chemical or physical stimulus, including the presence of a regulatory compound. Regulatory systems in prokaryotic systems would include the lac, tac, and trp operator systems.

Other examples of regulatory sequences are those which allow for gene amplification. In these cases, the nucleic acid sequence encoding the carbohydrate oxidase would be operably linked with the regulatory sequence.

While intracellular expression may be advantageous in some respects, e.g., when using certain bacteria as host cells, it is generally preferred that the expressed carbohydrate oxidase is secreted extracellularly.

Host Cells

The present invention also relates to recombinant host cells, either comprising a DNA construct or an expression vector as described above, which are advantageously used in the recombinant production of the carbohydrate oxidase. The host cell may be any progeny of a parent cell which is not identical to the parent cell due to mutations that occur during replication.

The cell is preferably transformed with a vector comprising a nucleic acid sequence followed by integration of the vector into the host chromosome. "Transformation" means introducing a vector comprising a nucleic acid sequence of the present invention into a host cell so that the vector is maintained as a chromosomal integrant or as a self-replicating extra-chromosomal vector. Integration is generally considered to be an advantage as the nucleic acid sequence is more likely to be stably maintained in the cell. Integration of the vector into the host chromosome occurs by homologous or non-homologous recombination as described above.

The choice of a host cell will to a large extent depend upon the gene encoding the carbohydrate oxidase and its source. The host cell may be a cell of a higher organism, such as a mammal or an insect, but is preferably a microbial cell, e.g., a bacterial or a fungal (including yeast) cell.

Examples of suitable bacterial cells are gram positive bacteria including, but not limited to, a Bacillus cell, e.g., *Bacillus alkalophilus, Bacillus amyloliquefaciens, Bacillus brevis, Bacillus circulans, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis*; or a Streptomyces cell, e.g., *Streptomyces lividans* or *Streptomyces murinus*, or gram negative bacteria such as *E. coli* and Pseudomonas sp. In a preferred embodiment, the bacterial host cell is a *Bacillus lentus, Bacillus licheniformis, Bacillus stearothermophilus* or *Bacillus subtilis* cell.

The transformation of a bacterial host cell may, for instance, be effected by protoplast transformation (see, e.g., Chang and Cohen, 1979, Molecular General Genetics 168:111–115), by using competent cells (see, e.g., Young and Spizizin, 1961, Journal of Bacteriology 81:823–829, or Dubnau and Davidoff-Abelson, 1971, Journal of Molecular Biology 56:209–221), by electroporation (see, e.g., Shigekawa and Dower, 1988, Biotechniques 6:742–751), or by conjugation (see, e.g., Koehler and Thorne, 1987, Journal of Bacteriology 169:5771–5278).

The host cell may also be a eukaryote, such as a mammalian cell, an insect cell, a plant cell or a fungal cell. Useful mammalian cells include Chinese hamster ovary (CHO) cells, HeLa cells, baby hamster kidney (BHK) cells, COS cells, or any number of other immortalized cell lines available, e.g., from the American Type Culture Collection.

In a preferred embodiment the host cell is a fungal cell. "Fungi," as used herein, includes the phyla Ascomycota, Basidomycota, Chytridiomycota, and Zygomycota (as defined by Hawksworth, et al., Ainsworth and Bisby's Dictionary of The Fungi, 8th edition, 1995, CAB International, University Press, Cambridge, UK) as well as the Oomycota (as cited in Hawksworth, et al., 1995, supra, page 171) and all mitosporic fungi (Hawksworth, et al., 1995, supra). Representative groups of Ascomycota include, e.g., Neurospora, Eupenicillium (=Penicillium), Emericella (=Aspergillus), Eurotium (=Aspergillus), and the true yeasts listed above. Examples of Basidiomycota include mushrooms, rusts, and smuts. Representative groups of Chytridiomycota include, e.g., Allomyces, Blastocladiella, Coelomomyces, and aquatic fungi. Representative groups of Oomycota include, e.g., Saprolegniomycetous aquatic fungi (water molds) such as Achlya. Examples of mitosporic fungi include Aspergillus, Penicillium, Candida, and Alternaria. Representative groups of Zygomycota include, e.g., Rhizopus and Mucor.

In a preferred embodiment, the fungal host cell is a yeast cell. "Yeast" as used herein includes ascosporogenous yeast (Endomycetales), basidiosporogenous yeast, and yeast belonging to the Fungi Imperfecti (Blastomycetes). The ascosporogenous yeasts are divided into the families Spermophthoraceae and Saccharomycetaceae. The latter is comprised of four subfamilies, Schizosaccharomycoideae (e.g., genus Schizosaccharomyces), Nadsonioideae, Lipomycoideae, and Saccharomycoideae (e.g., genera Pichia, Kluyveromyces and Saccharomyces). The basidiosporogenous yeasts include the genera Leucosporidim, Rhodosporidium, Sporidiobolus, Filobasidium, and Filobasidiella. Yeast belonging to the Fungi Imperfecti are divided into two families, Sporobolomycetaceae (e.g., genera Sorobolomyces and Bullera) and Cryptococcaceae 6 (e.g., genus Candida). The yeast may be as described in Biology and Activities of Yeast (Skinner, F. A., Passmore, S. M., and Davenport, R. R., eds, Soc. App. Bacteriol. Symposium Series No. 9, 1980. The biology of yeast and manipulation of yeast genetics are well known in the art (see, e.g., Biochemistry and Genetics of Yeast, Bacil, M., Horecker, B. J., and Stopani, A. O. M., editors, 2nd edition, 1987; The Yeasts, Rose, A. H., and Harrison, J. S., editors, 2nd edition, 1987; and The Molecular Biology of the Yeast Saccharomyces, Strathern et al., editors, 1981).

In a more preferred embodiment, the yeast host cell is a cell of a species of Candida, Kluyveromyces, Saccharomyces, Schizosaccharomyces, Pichia, or Yarrowia.

In a most preferred embodiment, the yeast host cell is a *Saccharomyces carlsbergensis, Saccharomyces cerevisiae, Saccharomyces diastaticus, Saccharomyces douglasii, Saccharomyces kluyveri, Saccharomyces norbensis* or *Saccharomyces oviformis* cell. In another most preferred embodiment, the yeast host cell is a *Kluyveromyces lactis* cell. In another most preferred embodiment, the yeast host cell is a *Yarrowia lipolytica* cell.

In a preferred embodiment, the fungal host cell is a filamentous fungal cell. "Filamentous fungi" include all filamentous forms of the subdivision Eumycota and Oomycota (as defined by Hawksworth et al., 1995, supra). The filamentous fungi are characterized by a vegetative mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as Saccharomyces cerevisiae is by budding of a unicellular thallus and carbon catabolism may be fermentative. In a more preferred embodiment, the filamentous fungal host cell is a cell of a species of, but not limited to, Acremonium, Aspergillus, Fusarium, Humicola, Mucor, Myceliophthora, Neurospora, Penicillium, Thielavia, Tolypocladium, and Trichoderma.

In a most preferred embodiment, the filamentous fungal host cell is an *Aspergillus awamori, Aspergillus foetidus, Aspergillus japonicus, Aspergillus nidulans, Aspergillus niger* or *Aspergillus oryzae* cell. In another most preferred embodiment, the filamentous fungal host cell is a *Fusarium cerealis, Fusarium crookwellense, Fusarium graminearum, Fusarium oxysporum, Fusarium sambucinum, Fusarium sulphureum,* or *Fusarium venenatum* cell. In another most preferred embodiment, the filamentous fungal host cell is a *Humicola insolens* or *Humicola lanuginosa* cell. In another most preferred embodiment, the filamentous fungal host cell is a *Mucor miehei* cell. In another most preferred embodiment, the filamentous fungal host cell is a *Myceliophthora thermophilum* cell. In another most preferred embodiment, the filamentous fungal host cell is a *Neurospora crassa* cell. In another most preferred embodiment, the filamentous fungal host cell is a *Penicillium purpurogenum* cell. In another most preferred embodiment, the filamentous fungal host cell is a *Thielavia terrestris* cell. In another most preferred embodiment, the Trichoderma cell is a *Trichoderma harzianum, Trichoderma koningii, Trichoderma longibrachiatum, Trichoderma reesei* or *Trichoderma viride* cell.

Fungal cells may be transformed by a process involving protoplast formation, transformation of the protoplasts, and regeneration of the cell wall in a manner known per se. Suitable procedures for transformation of Aspergillus host cells are described in EP 238 023 and Yelton et al., 1984, Proceedings of the National Academy of Sciences USA 81:1470–1474. A suitable method of transforming Fusarium species is described by Malardier et al., 1989, Gene 78:147–156 or in copending U.S. Ser. No. 08/269,449. Yeast may be transformed using the procedures described by Becker and Guarente, in Abelson, J. N. and Simon, M. I., editors, "Guide to Yeast Genetics and Molecular Biology", Methods in Enzymology, Volume 194, pp 182–187, Academic Press, Inc., New York; Ito, et al., 1983, Journal of Bacteriology 153:163; and Hinnen et al., 1978, Proceedings of the National Academy of Sciences USA 75:1920. Mammalian cells may be transformed by direct uptake using the calcium phosphate precipitation method of Graham and Van der Eb (1978, Virology 52:546).

Recombinant Methods of Production

The carbohydrate oxidase can be produced by recombinant methods comprising cultivating a host cell as described above under conditions conducive to the production of said carbohydrate oxidase and recovering the carbohydrate oxidase from the cells and/or culture medium.

In these methods, the cells are cultivated in a nutrient medium suitable for production of the carbohydrate oxidase using methods known in the art. For example, the cell may be cultivated by shake flask cultivation, small-scale or large-scale fermentation (including continuous, batch, fedbatch, or solid state fermentations) in laboratory or industrial fermentors performed in a suitable medium and under conditions allowing the carbohydrate oxidase to be expressed and/or isolated. The cultivation takes place in a suitable nutrient medium comprising carbon and nitrogen sources and inorganic salts, using procedures known in the art (see, e.g., M. V. Arbige et al., in Abraham L. Sonenshein, James A. Hoch, and Richard Losick, editors, *Bacillus subtilis* and Other Gram-Positive Bacteria, American Society For Microbiology, Washington, D.C., 1993, pages 871–895). Suitable media are available from commercial suppliers or may be prepared ac-cording to published compositions (e.g., in catalogues of the American Type Culture Collection). If the carbohydrate oxidase is secreted into the nutrient medium, the carbohydrate oxidase can be recovered directly from the medium. If the carbohydrate oxidase is not secreted, it is re-covered from cell lysates.

The carbohydrate oxidase may be detected using methods known in the art that are specific for the polypeptide. These detection methods may include use of specific anti-bodies, formation of an enzyme product, or disappearance of an enzyme substrate. For example, an enzyme assay may be used to determine the activity of the polypeptide.

The resulting carbohydrate oxidase may be recovered by methods known in the art. For example, the carbohydrate oxidase may be recovered from the nutrient medium by conventional procedures including, but not limited to, centrifugation, filtration, extraction, spray-drying, evaporation, or precipitation.

The carbohydrate oxidase of the present invention may be purified by a variety of procedures known in the art including, but not limited to, chromatography (e.g., ion ex-change, affinity, hydrophobic, chromatofocusing, and size exclusion), electrophoretic procedures (e.g., preparative isoelectric focusing (IEF), differential solubility (e.g., ammonium sulfate precipitation), or extraction (see, e.g., Protein Purification, J.-C. Janson and Lars Ryden, editors, VCH Publishers, New York, 1989).

Industrial Applications

In addition to the us in baking, discussed above, the carbohydrate oxidase may be used, for example, in personal care products such as toothpaste, in particular, where whitening of the teeth is desirable, mouthwash, denture cleaner, liquid soap, skin care creams and lotions, hair care and body care formulations, and solutions for cleaning contact lenses in an amount effective to act as an antibacterial agent. The carbohydrate oxidase may also be a component of a laundry detergent composition or a dishwashing detergent composition and may be used for the generation of hydrogen peroxide. The laundry detergent composition may comprise a surfactant, said carbohydrate oxidase and a substrate for the carbohydrate oxidase. The dishwashing detergent composition may comprise said carbohydrate oxidase and a bleach precursor or peroxy acid, and a substrate for carbohydrate oxidase.

The carbohydrate oxidase may be used as an analytical reagent, for example, to determine the amount of reducing sugars present in a given sample, or the enzyme may be immobilized and inserted into an electrode to provide continuous measurement of starch or cellulose hydrolysis.

In addition, the carbohydrate oxidase of the present invention may be used to oxidize an oligosaccharide with a glucose residue at the reducing end into the corresponding acid, e.g. to produce lactobionic acid from lactose.

Methods for Determination of Carbohydrate Oxidase Activity

DMAB/MBTH Assay

Premix:

7.2 mM 3-dimethylaminobenzoic acid (DMAB)

0.33 mM 3-methyl-2-benzothiazolinone hydrazone (MBTH)

4 mg/ml recombinant *Coprinus cinereus* peroxidase (rCiP)

0.4M/0.4M Phosphate/Citrate buffer (pH 6)

Incubation mix:

180 $\mu$l 500 mM glucose 25 mM citrate 25 mM phosphate pH 6.0

20 $\mu$l Sample

The incubation mix is allowed to incubate for 20 minutes at 30° C. Then 100 ml of the incubation mix and 100 ml premix are mixed together. After 30 seconds, the absorbance at 540 (or 490) nm is read. A standard of 0.2 mM H2O2 is included.

4AA-TOPS Assay

Assays are carried out in 96 well microtiter plates. 100 μl 0.1 M phosphate/citrate, pH 6 is mixed with 50 μl 0.24 M glucose and 50 μl pre-mix (3 mM 4-aminoantipyrine (4AA), 7 mM N-ethyl-N-sulfopropyl-m-toluidine (TOPS), 40 PODU/ml rCiP) and the reaction is started by adding 40 μl of oxidase solution diluted appropriately. Absorption is measured at 490 nm as a function time using the Vmax microtiter plate ready from Molecular Devices and the activity is taken as the slope of the linear increase in absorption.

EXAMPLES

Example 1

Production of Carbohydrate Oxidase from Wild-type *M. nivale*

Cultivation of *M. nivale*

A strain of *M. nivale*, CBS 100236, was fermented using the following complete medium:

| Shaking flask medium: | BA |
|---|---|
| Rofec (Roquette) | 10 gram |
| $NH_4NO_3$ (Merck) | 10 gram |
| $KH_2PO_4$ (Merck) | 10 gram |
| Solcafloc (Dicacel) | 40 gram |
| $MgSO_4$—7($H_2O$) | 0.75 gram |
| Pluronic 100% (BASF) | 0.1 ml |
| Tap water for a final volume of 1000 ml | |

The pH was adjusted to pH 6.5, then 1 tablet of 500 mg $CaCO_3$ was added. One hundred ml of the complete medium was added to each 500 ml 2-baffle shake flask. The shake flasks were then autoclaved for 40 min. at 121° C. An inoculum was prepared from a spore suspension prepared from 5 PDA slants, grown for 7 days at 26° C., then washed in 20 ml sterile water and Tween 80 (ICI). Each shake flask was inoculated with 2 ml of the spore suspension, then cultured for 10 days at 26° C. and with constant shaking at 125 rpm. At the end of cultivation, the cells were pelleted, and the enzyme was purified from the supernatant.

Purification

From a 5 liter fermentation, 4300 ml of centrifuged fermentation broth was filtered and concentrated to 660 ml by ultrafiltration using a filter with a molecular weight cutoff of 10 kDa (Filtron). The enzyme was precipitated with $(NH4)_2SO_4$ between 200 and 400 mg/ml. After dissolving the precipitate in 25 mM Tris pH 7.5 the sample was washed by ultrafiltration until the conductivity was identical to 25 mM Tris pH 7.5. The sample was passed over a column of 300 ml Q-Sepharose XL (Pharmacia) equilibrated in the same buffer and the run-through collected. After adding $(NH4)_2SO_4$ to 100 mg/ml the sample was passed over a HIC column (Toyopearl-butyl 650) (TosoHaas) equilibrated with 25 mM Tris pH 7.5; 100 mg $(NH4)_2SO_4$ /ml. The run-through was washed with 25 mM acetate buffer pH 5.0 and applied to a column of SP-Sepharose (Pharmacia) equilibrated in the same buffer. Bound enzyme was eluted using a linear salt gradient to 1 M NaCl in 25 mM acetate buffer pH 5.0 over 10 column volumes. Active fractions were pooled. Final polishing of the preparation was done by HIC chromatography on a phenyl-superose column, using a buffer of 25 mM acetate buffer pH 5.0 with a linear gradient running from 2 M $(NH4)_2SO_4$ to 0 M over 20 column volumes. Active fractions were pooled and dialyzed against 25 mM acetate buffer pH 5.0 for 24 hours.

Characterization

Analysis of the purified protein by SDS-PAGE indicated a molecular weight of approximately 52 kDa and a pI of around 8.9 by isoelectric focusing.

The purified *M. nivale* oxidase also showed a pronounced yellow color, suggesting the presence of FAD as a cofactor. An absorbance scan of the enzyme revealed two absorption maxima, at 385 and 440 nm, characteristic of the presence of FAD in the enzyme. In the presence of glucose, the peak at 440 nm disappeared, indicating a reduction of the FAD.

Example 2

Amino Acid Sequences from *M. nivale* Carbohydrate Oxidase

A highly purified preparation of *M. nivale* was reduced and alkylated. A sample of the enzyme was then degraded with Lysyl-endopeptidase (Wako) or TPCK-trypsin (Promega). Peptides were isolated by RP-HPLC on a Vydac 218TP column (Vydac) in TFA (trifluoroacetate)/isopropanol and repurified on a Vydac 218TP column in TFA/acetonitrile. Selected peptides were analyzed by Edman degradation. The N-terminal sequence was determined by sequencing the purified enzyme electroblotted onto a PVDF membrane.

The partial sequences obtained were an N-terminal sequence shown at positions 1–24 of SEQ ID NO: 2 and internal sequences as shown at positions 229–266, 249–271, 303–322, 336–347, 383–404, 405–414, 420–440 of SEQ ID NO: 2. None of the sequences from the carbohydrate oxidase showed homology to any relevant sequences when searched against the Swissprot and EMBL databases.

Example 3

Extraction of *Microdochium nivale* Genomic DNA

Agar slants of *Microdochium nivale* (NN008551, CBS 100236) mycelia were rinsed with 10 ml of sterile 0.008% Tween 20. A 2 ml volume of the mycelial solution was inoculated into a 250 ml shake flask containing 50 ml of MY50 pH 6.0 medium. The MY50 pH 6.0 medium was composed per liter of 50 g of maltodextrin, 2 g of $MgSO_4.7H_2O$, 10 g of $KH_2PO_4$, 2 g of $K_2SO_4$, 2 g of citric acid, 10 g of yeast extract, 2 g of urea, and 0.5 ml of AMG trace elements. The AMG trace metals solution was composed per liter of 14.3 g of $ZnSO_4.7H_2O$, 2.5 g of $CuSO_4.5H_2O$, 0.5 g of $NiCl_2.6H_2O$, 13.8 g of $FeSO_4.7H_2O$, 8.5 g of $MnSO_4.H_2O$, and 3 g of citric acid. The shake flask was incubated at 26° C., 125 rpm for 6 days.

Mycelia from the 6 day culture were collected through Miracloth (Calbiochem, La Jolla, Calif.), rinsed twice with approximately 50 ml of 10 mM Tris-1 mM EDTA pH 8.0 (TE), and squeezed dry. The mycelia were then frozen in liquid nitrogen and ground to a fine powder in an electric coffee grinder pre-chilled with dry ice. A 2 g sample of the powder was transferred to a sterile disposable 50 ml conical tube and a 20 ml volume of lysis buffer (100 mM EDTA, 10 mM Tris, 1% Triton X-100, 500 mM guanidine-HCl, 200 mM NaCl, pH 8.0) was added slowly followed by 20 μg of DNase-free RNase A per ml. The mixture was incubated at 37° C. for 30 minutes. Proteinase K was then added at 0.8 mg per ml and the mixture was incubated at 50° C. for an additional 2 hours. The lysed mixture was centrifuged at 12–15,000×g for 20 minutes to pellet the insoluble debris.

The lysate supernatant was transferred to a Qiagen-tip 500 Maxi column (Qiagen, Santa Clarita, Calif.) pre-equilibrated with 10 ml of QBT buffer (Qiagen, Santa Clarita, Calif.) and the column was washed with 30 ml of QC buffer (Qiagen, Santa Clarita, Calif.). The DNA was eluted with 15 ml QF buffer (Qiagen, Santa Clarita, Calif.) and 7 volumes of filter sterilized isopropanol was added to the eluted DNA solution. The solution was mixed gently and then centrifuged for 20 minutes at 15,000×g to pellet the DNA. The pelleted DNA was washed with ml of ice-cold 70% ethanol, air dried, and re-suspended in 500 µl of TE.

Example 4
PCR Amplification of *Microdochium nivale* Carbohydrate Oxidase Gene

The primary amino acid sequence data from the N-terminal and internal fragments of the purified *Microdochium nivale* carbohydrate oxidase described in Example 2 was used to create the following degenerate PCR primers to amplify the carbohydrate oxidase gene from the genomic *Microdochium nivale* DNA prepared in Example 3:

Forward primer (N-terminal peptide sequence): GCIGCIG-GIGTICCIATHGAYAT (SEQ ID NO:3)

Reverse Primer (internal peptide sequence): IGGRTCIGCR-TARTTDATRTACAT (SEQ ID NO:4)

Amplification was accomplished using the Hot Wax Optistart™ Kit (Invitrogen, San Diego, Calif.) according to the manufacturer's instructions. Six reactions were set up that differ from each other by pH and $Mg^{2+}$ concentration as shown below in the following table:

| | 1.5 mM $MgCl_2$ | 2.5 mM $MgCl_2$ | 3.5 mM $MgCl_2$ |
|---|---|---|---|
| pH 8.5 | reaction 1 | reaction 2 | reaction 3 |
| pH 9 | | reaction 4 | |
| pH 9.5 | | reaction 5 | |
| pH 10 | | reaction 6 | |

The amplification reactions (50 μl) contained 1.62 μg of *Microdochium nivale* genomic DNA as the template, 50 pmole of each primer, 1×PCR Buffer, 5 μl of a 10 mM dNTP mix, and a HotWax™ $Mg^{2+}$ bead containing the appropriate amount of $Mg^{2+}$. The reactions were cycled in a Perkin Elmer 480 Thermal Cycler programmed as follows: Cycle 1 at 94° C. for 2.5 minutes and 72° C. for 2 minutes; cycles 2–37 each at 94° C. for 45 seconds, 50° C. for 45 seconds, and 72° C. for 2 minutes; and cycle 38 a 94° C. for 45 seconds, 50° C. for 45 seconds, and 72° C. for 10 minutes. Cycle 39 was a 4° C. soak cycle.

A 9 μl volume from each reaction was electrophoresed on a 1% agarose gel using 50 mM Tris-50 mM boric acid-1 mM EDTA (TBE) buffer. Reactions 4, 5, and 6 revealed a major band at 1335 bp. Reactions 4, 5, and 6, were pooled and electrophoresed on a 1% agarose gel as before. The 1335 bp band was excised from the gel and purified using a Qiaex II Gel Extraction Kit (Qiagen, Santa Clarita, Calif.). The purified 1335 bp PCR product was then cloned into pCR2.1-TOPO (Invitrogen, San Diego, Calif.) and transformed into *Escherichia coli* TOP10 cells (Invitrogen, Carlsbad, Calif.) according to the manufacturer's instructions. Plasmid DNA was isolated from the transformants using a Wizard Maxi Prep Kit (Promega, Madison, Wis.). The isolated plasmid DNA was sequenced using an Applied Biosystems Prism 377 DNA Sequencer and 377XL collection and analysis software (Perkin Elmer, Applied Biosystems, Foster City, Calif.) according to the manufacturer's instructions. The sequence data confirmed that the 1335 bp fragment encoded part of the *Microdochium nivale* carbohydrate oxidase gene.

Example 5

Southern Blot of *Microdochium nivale* Genomic DNA

A sample of the genomic DNA prepared in Example 3 was analyzed by Southern hybridization (Maniatis et al., 1982, *Molecular Cloning, a Laboratory Manual*, Cold Spring Harbor Press, Cold Spring Harbor, N.Y.). Approximately 3 μg of the genomic DNA were digested with EcoRI, KpnI, NotI, SacI, SphI, or XbaI (Boehringer Mannheim, Indianapolis, Ind.) and fractionated by size on a 0.6% agarose gel using TBE buffer. The gel was photographed under short wavelength UV light and soaked for 30 minutes in 0.5 M NaOH-1.5 M NaCl followed by 15 minutes in 1 M Tris-HCl pH 8–1.5 M NaCl. DNA in the gel was transferred onto a Hybond N hybridization membrane (Amersham Life Science, Arlington Heights, Ill.) by capillary blotting in 20×SSPE (3 M sodium chloride-0.2 M sodium dibasic phosphate-0.02 M disodium EDTA) using the Turbo Blot method (Schleicher and Schuell, Keene, N.H.). The membrane was crosslinked with UV (UV Stratalinker 2400, Stratagene, La Jolla, Calif.) and then soaked for 2 hours in the following hybridization buffer at 45° C. with gentle agitation: 5×SSPE, 50% formamide (v/v), 0.3% SDS, and 200 μg/ml denatured and sheared salmon testes DNA.

The 1335 bp fragment described in Example 4, containing part of the coding sequence of the *Microdochium nivale* carbohydrate oxidase, was radiolabeled by random priming (Prime it II, Stratagene, La Jolla, Calif.) with $\alpha[^{32}P]$dCTP (Amersham, Arlington Heights, Ill.). The $\alpha[^{32}P]$dCTP-labeled fragment was added to the hybridization buffer at an activity of approximately $1\times10^6$ cpm per ml of buffer. The mixture was incubated with the membrane overnight at 45° C. in a shaking water bath. Following incubation, the membrane was washed three times for fifteen minutes each in 2×SSC (0.3 M NaCl, 30 mM sodium citrate pH 7.0) with 0.2% SDS at 45° C. The membrane was dried on a paper towel for 15 minutes, then wrapped in plastic wrap, and exposed to X-ray film for three hours at −70° C. with intensifying screens (Kodak, Rochester, N.Y.).

The Southern blot showed the presence of a 3 kb band in the lane containing the SacI digest. Since the SacI digest yielded a band size small enough to amplify and large enough to contain the full-length gene, it was used for isolating the complete gene by inverse PCR.

Example 6

Inverse PCR of Coding Sequence of the *Microdochium nivale* Carbohydrate Oxidase Gene Inverse PCR was used to obtain the 5' and 3' flanking DNA of the 1335 bp fragment to isolate the entire coding sequence of the *Microdochium nivale* carbohydrate oxidase gene. A 6 μg sample of *Microdochium nivale* genomic DNA (Example 3) was digested to completion with SacI and then purified using the QIAquick Nucleotide Removal Kit (Qiagen, Santa Clarita, Calif.) according to the manufacturer's instructions. A 1 μg sample of the purified digested DNA was self-ligated overnight at 14–16° C. with 10 units of T4 Ligase (Boehringer Mannheim, Indianapolis, Ind.) and 1×ligase buffer in a final volume of 500 μl. The ligase was then heat inactivated by incubating the reaction at 65° C. for 15 minutes. The reaction was concentrated using a Microcon 30 (Millipore, Bedford, Mass.). The reaction products were purified using the QIAquick Nucleotide Removal Kit. The self-ligated products were then used as a template for inverse PCR.

The following primers were created to the 5' and 3' ends of the carbohydrate oxidase gene, in the opposite direction to those in conventional PCR, to amplify out from the known region of the 1335 bp PCR product:

Upper 1199 bp: TCCAGTTCTACGACCGCTACG (SEQ ID NO:5)

Lower 158 bp: CAGACTTGGCAGAGACCTTGA (SEQ ID NO:6)

The amplification reaction (100 μl) contained 100 pmoles of each primer, 1 μg of the SacI digested and self-ligated genomic DNA, 10 μl of a 10 mM dNTP mix, 1×Taq polymerase buffer (Perkin Elmer, Foster City, Calif.), and 5 units of Taq polymerase (Perkin Elmer, Foster City, Calif.). Sterile mineral oil was layered on top of the reaction and placed in a Perkin Elmer Model 480 Thermal Cycler programmed as follows: Cycle 1 at 94° C. for 2.5 minutes and 72° C. for 2 minutes; cycles 2–11 each at 94° C. for 30 seconds, 55° C. for 45 seconds, and 72° C. for 2 minutes; cycles 12–28 each at 94° C. for 30 seconds, 55° C. for 45 seconds, and 72° C. for 2 minutes with an extension of 20 seconds per cycle; and cycle 29 at 72° C. for 10 minutes. Cycle 30 was a 4° C. soak cycle.

The reaction was electrophoresed on a 1% agarose gel using TBE buffer revealing a 3 kb band. The 3 kb band was excised from the gel and purified using a Qiaex II Gel Extraction Kit. The purified 3 kb PCR product was then cloned into pCR2.1-TOPO and transformed into *Escherichia coli* TOP10 cells to generate *Eschelichla coli* pEJG40/TOP10. The transformant *E. coli* pEJG40/TOP10 was deposited according to the Budapest Treaty on the International Recognition of the Deposits of Microorganisms for the Purpose of Patent Procedures on Jun. 12, 1998 at the Agricultural Research Service Collection (NRRL), 1815 North University Street, Peoria, Ill., and designated NRRL B-30034.

Plasmid DNA was isolated from the transformant using a Wizard Maxi Prep Kit. The isolated plasmid DNA was sequenced using an Applied Biosystems Prism 377 DNA Sequencer and 377XL collection and analysis software according to the primer walking technique with dye-terminator chemistry (Giesecke et al., 1992, *Journal of Virol. Methods* 38: 47–60). In addition to the lac-forward and lac-reverse primers, the following oligonucleotide sequencing primers were used for sequencing:

Sequencing Primers for 1335 bp fragment:

| | |
|---|---|
| IACRTCRMRTARTARTCIACRAARTT | (SEQ ID NO:7) |
| RTTIACCCAICCRTC | (SEQ ID NO:8) |
| IGGRTCIGCRTARTTDATRTACAT | (SEQ ID NO:9) |
| DATRAARTCIACRTGRTCRAARTT | (SEQ ID NO:10) |
| CCAYTGYTCIGGIGTICCRTARTA | (SEQ ID NO:11) |
| CTCGCCACTTTCCCTGCTCCC | (SEQ ID NO:12) |
| CTCGGTCACCAAGGCTCTCCC | (SEQ ID NO:13) |
| GACCGCTACGACMCMCCAG | (SEQ ID NO:14) |

Sequencing primers for Inverse PCR product:

| | |
|---|---|
| TCGGAGAAATGAGAGCMCCA | (SEQ ID NO:15) |
| AGCCGACGTCCAGCATAGCAG | (SEQ ID NO:16) |
| ACCCTACCATACGAGTTCACG | (SEQ ID NO:17) |
| GGTCGAATCGTCACAAAGTAT | (SEQ ID NO:18) |
| CACTGGACTGCCGACTGGATG | (SEQ ID NO:19) |
| CACMCMCCAGACCTACCC | (SEQ ID NO:20) |
| CTCAGCAGCACTTCTTTTCAT | (SEQ ID NO:21) |

Sequencing revealed a nucleic acid sequence with an open reading frame (ORF) of 1448 bp (SEQ ID NO:1) containing one intron of 65 bp. The G+C content of this ORF is 58.33%. The −3 position of the translational start is an adenine agreeing with Kozak's rules in which the −3 position is always an adenine. A putative TATA motif is also present at −122, TATAAA.

The deduced amino acid sequence (SEQ ID NO:2) demonstrated a protein of 495 amino acids with a calculated molecular weight of 54,678 daltons. Based on the rules of van Heijne (van Heijne, 1984, *Journal of Molecular Biology* 173: 243–251), the first 18 amino acids likely comprise a secretory signal peptide which directs the nascent polypeptide into the endoplasmic reticulum. A score of 30.395 was obtained using the van Heijne program to predict signal peptides. The amino acid sequences of the partial peptides derived from the purified *Microdochium nivale* carbohydrate oxidase fragments (Example 2) were consistent with those found in the deduced amino acid sequence except there may be a four amino acid propeptide in that the N-terminal amino acid sequence does not follow immediately after the signal peptide.

Example 7

Construction of *Microdochium nivale* Carbohydrate Oxidase Expression Vectors

Two synthetic oligonucleotide primers shown below were synthesized to PCR amplify the carbohydrate oxidase gene from *Microdochium nivale* genomic DNA for subcloning and expression in Fusarium and Aspergillus host cells. In order to facilitate the subcloning of the gene fragment into the expression vectors pDM181 and pBANE15, SwaI and PacI restriction enzyme sites were introduced at the 5' and 3' end of the carboxypeptidase gene, respectively.

Forward primer: 5'-GATTTAAATATGCGTTCTGCATTTATCTTG-3' (SEQ ID NO:22)

Reverse primer: 5'-GTTAATTMTTATTTGACAGGGCGGA-CAGC-3' (SEQ ID NO:23)

Bold letters (at positions 10–30 of each) represent coding sequence.

The PCR, purification, and subcloning were performed as described in Example 4 except the cycling parameters varied as follows: Cycle 1 at 94° C. for 2 minutes, 60° C. for 4 seconds, and 72° C. for 45 seconds; cycles 2–37 each at 94° C. for 45 seconds, 60° C. for 45 seconds, and 72° C. for 2 minutes; and cycle 38 at 94° C. for 45 seconds, 60° C. for 45 seconds, and 72° C. for 6 minutes. Cycle 39 was a 4° C. soak cycle.

The vector pDM181 contains the *Fusarium oxysporum* trypsin-like protease promoter and terminator as regulatory sequences and the *Streptomyces hygroscopicus* bar gene as a selectable marker for fungal transformations (WO 98/20136; de Block et al., 1987, *EMBO Journal* 6: 2513–2518). The vector pBANE15 (FIG. 1) contains the TAKA promoter and AMG terminator and the *Aspergillus nidulans* amdS gene as the selectable marker for fungal transformations. Both vectors also contain the amp gene for selection in *E. coli.*

The carbohydrate oxidase clone obtained above was digested with SwaI and PacI and purified by 0.8% agarose gel electrophoresis using TBE buffer and a Qiaex II Gel Extraction Kit. The digested fragment was cloned into pDM181 and pBANE15 previously digested with SwaI and PacI resulting in the expression plasmids pEJG35 and pEJG33, respectively (FIGS. 2 and 3).

The expression plasmids were transformed into *E. coli* XL10 Gold cells (Stratagene, La Jolla, Calif.). Transformants containing the correct plasmids were isolated and plasmid DNA was prepared using the Wizard Maxi Prep Kit.

Example 8
Expression of the *Microdochium nivale* Carbohydrate Oxidase Gene in *Aspergillus oryzae* pEJG33 was transformed into protease-deficient *Aspergillus oryzae* host strains JaL142 (Christensen et al., 1988, Bio/Technology 6: 1419–1422) and JaL228 (WO 98/12300) using protoplast transformation (Yelton et al., 1984, *Proceedings of the National Academy of Sciences USA* 81: 1470–1474). One hundred ill of protoplasts ($2\times10^6$) were placed into a 14 ml Falcon tube with ca. 5 µg of pEJG33 and gently mixed. A 250 µl volume of 60% PEG 4000 in 10 mM Tris-HCl pH 7.5–10 mM $CaCl_2$ was added and mixed by gentle rolling. The tube was then incubated at 37° C. for 30 minutes. Three ml of STC (1.2 M sorbitol, 10 mM Tris pH 7.5, 10 mM $CaCl_2$) was added and mixed by inversion. The solution was then plated directly onto Cove plates composed per liter of 342.3 g of sucrose, 10 ml of 1.5 M CsCl, 10 ml of 1 M acetamide, 20 ml of 1×Cove salt solution, and 1% agar. 5×Cove salts solution was composed per liter of 26 g of KCl, 26 g of $MgSO_4.7H_2O$, 76 g of $KH_2PO_4$, and 50 ml of Cove trace metals. The Cove trace metals solution was composed per liter of 0.04 g of $NaB_4O_7.10H_2O$, 0.4 g of $CuSO_4.5H_2O$, 1.2 g of $FeSO_4.7H_2O$, 0.7 g of $MnSO_4.H_2O$, 0.8 g of $Na_2MoO_2.2H_2O$, and 10 g of $ZnSO_4.7H_2O$. Plates were incubated 5 days at 37° C. Transformants were transferred to plates of the same medium and incubated 5 days at 37° C. The transformants were purified by streaking spores and picking isolated colonies using the same plates under the same conditions. Totally, 12 *Aspergillus oryzae* JaL142 transformants and 22 *Aspergillus oryzae* JaL228 transformants were recovered.

The transformants were grown on individual COVE plates as above, and then tested for carbohydrate oxidase activity using an indicator plate described by WiHeveen et al. (1990, *Applied Microbial Biotechnology* 33: 683). The untransformed hosts were used as controls. A total of 11 positive transformants were identified. Spore stocks of each positive transformant were made with sterile deionized water. A 500 µl volume of each spore stock including the untransformed host was inoculated into 125 ml shake flasks containing 25 ml of MY50 medium. The shake flasks were incubated at 37° C., 200 rpm for 7 days. Since the *Microdochium nivale* carbohydrate oxidase contains FAD as a cofactor, one set of flasks also contained 52 µM riboflavin 5'-phosphate (Sigma Chemical Co., St. Louis, Mo.).

Samples of 500 µl were removed at days 3, 5, and 7 from each flask and assayed for carbohydrate oxidase activity. Carbohydrate oxidase activity was measured in a 96 well plate containing 10 µl of supernatant followed by the addition of 1 µl of o-anisidine, 69 µl of Britton and Robinson buffer pH 6.0, 10 µl of 1 M D-glucose, and 10 µl of *Coprinus cinereus* peroxidase (3.76 PODU/ml), obtained as described in WO 92/16634. The activity was measured at 405 nm for 10 minutes in mOD/min. The transformants all produced detectable carbohydrate oxidase activity. The addition of riboflavin 5'-phosphate to the shake flasks had a minor effect on increasing activity. Samples of 20 µl from the highest carbohydrate oxidase producers were run on an 8–16% Tris-Glycine gel (Novex, San Diego, Calif.) which confirmed the production of carbohydrate oxidase.

The transformants with the highest activities were spore purified by patching isolated colonies onto new COVE plates twice in succession and then regrown in shake flasks and retested for carbohydrate oxidase activity as above to confirm production of the carbohydrate oxidase.

Fermentations of *Aspergillus oryzae* JaL228 containing pEJG33 were run at 34° C., pH 7, 1000–1200 rpm for 8 days in 2 liter lab fermentors containing medium composed of Nutriose, yeast extract, $(NH_4)_2HPO_4$, $MgSO_4.7H_2O$, citric acid, $K_2SO_4$, $CaCl_2.H_2O$, and trace metals solution. The trace metals solution (1000×) was composed per liter of 22 g of $ZnSO_4.7H_2O$, 11 g of $H_3BO_3$, 5 g of $MnCl_2.4H_2O$, 5 g of $FeSO_4.7H_2O$, 1.6 g of $CoCl_2.5H_2O$, 1.6 g of $(NH_4)_6Mo_7O_{24}$, and 50 g of $Na_4EDTA$. One fermentation was supplemented with $2\times10^{-4}$ M FMN per liter (GOX003.8) while the other one was not (GOX002.8).

Eight day samples were assayed as described above. The results showed the presence of carbohydrate oxidase activity in both fermentations, but no difference in carbohydrate oxidase activity was detected between the two fermentation broths.

Example 9
Expression of the *Microdochium nivale* Carbohydrate Oxidase Gene in *Fusarium venenatum* pEJG35 was introduced into *Fusarium venenatum* strain CC1-3 (WO 97/26330) using the method of Royer et al. (1995, *Bio/Technology* 13: 1479–1483) with BASTA™ (phosphinothricin resistance selection). The active ingredient in the herbicide BASTA™ is phosphinothricin. BASTA™ was obtained from AgrEvo (Hoechst Schering, Rodovre, Denmark) and was extracted twice with phenol:chloroform:isoamyl alcohol (25:24:1), and once with chloroform:isoamyl alcohol (24:1) before use. Based on growth in the presence of BASTA™, 14 transformants were recovered and then grown at room temperature on individual agar plates composed of 20 ml of 5×Vogels medium (Royer et al., 1995, supra), 25 g of sucrose, 25 g of noble agar, and 25 mM $NaNO_3$ supplemented with mg of BASTA™ per ml. The transformants were then tested for carbohydrate oxidase production using an indicator plate described by WiHeveen et al., 1990, supra. Five transformants tested positive. A plug from each positive transformant including untransformed *Fusarium venenatum* CC1-3 as a control were inoculated into individual 125 ml shake flasks containing 30 ml of M400Da medium supplemented with 0.5 g of $CaCl_2$ per liter and incubated at 30° C., for 7 days under 150 rpm agitation. The M400Da medium was composed per liter of 50 g of maltodextrin, 2 g of $MgSO_4$, 2 g of $KH_2PO_4$, 4 g of citric acid, 2 g of urea, 0.5 g of $CaCl_2$, and 1 ml of Cove trace metals. One set of flasks also contained 52 µM riboflavin 5'-phosphate.

At days 3, 5, and 7, 500 µl of culture broth was removed from each flask and centrifuged. The supernatants were assayed for carbohydrate oxidase activity as described in Example 8. The transformants all produced detectable carbohydrate oxidase activity. The addition of riboflavin 5'-phosphate to the shake flasks had essentially no effect on increasing activity. Samples of 20 µl from the highest carbohydrate oxidase producers were run on an 8–16% Tris-Glycine gel (Novex, San Diego, Calif.), which confirmed the production of carbohydrate oxidase. The highest producers were spore purified on Vogels/BASTA™ plates.

A fermentation of *Fusarium venenatum* strain CC1-3 containing pEJG35 was run at 30° C. for 8 days in a 2 liter fermentor containing medium composed per liter of 20 g of sucrose, 2.0 g of $MgSO_4.7H_2O$, 2.0 of $KH_2PO_4$, 2.0 of citric acid.$H_2O$, 2.0 g of $CaCl_2.2H_2O$, 0.5 ml of AMG trace metals (pH adjusted to 4.5 prior to sterilization), and a filter sterilized mixture composed per liter of 2.5 g of urea and 30 ml of a soy vitamin mixture, which was added after sterilization and cooling of the medium. Feed streams were batched autoclaved mixtures composed of sucrose and urea.

Eight day samples were assayed as described in Example 8. The results showed the presence of carbohydrate oxidase activity.

Example 10

Purification of recombinant *Microdochium nivale* Carbohydrate Oxidase

The two *Aspergillus oryzae* JAL228 fermentation JaL228 broths, GOX002.8 (1.2 l) and GOX003.8 (1.4 l), prepared as described in Example 8 were combined. The combined broths were filtered using Whatman #2 filter paper and then washed and concentrated by ultrafiltration to 512 ml using an Amicon Spiral-Concentrator equipped with a S1Y10 membrane. Measurement of carbohydrate oxidase activity as described in Example 8 indicated essentially 100% recovery of the enzyme.

The concentrate was then loaded onto a Q-Sepharose column (189 ml; Pharmacia Biotech, Inc., Piscataway, N.J.) pre-equilibrated with 10 mM Tris-HCl pH 8. The carbohydrate oxidase was eluted with 2 M NaCl in 10 mM Tris-HCl pH 8. Measurement of carbohydrate oxidase activity as described above indicated most of the enzyme did not bind to the column.

The flow-through fraction (760 ml) from the Q-Sepharose column was adjusted to pH 5.5 and loaded onto a SP-Sepharose column (176 ml; Pharmacia Biotech, Inc., Piscataway, N.J.) pre-equilibrated with 10 mM MES pH 5.5. The carbohydrate oxidase was eluted with 1 M NaCl in 10 mM MES pH 5.5, which yielded a carbohydrate oxidase preparation with apparent electrophoretic purity by SDS-PAGE. The table below summarizes the purification of the recombinant carbohydrate oxidase. Overall a 14-fold purification with a 31% recovery was achieved based on the following oxygen electrode assay. Carbohydrate oxidase was measured using a Hansatech $O_2$ electrode with an assay solution composed of 0.26 ml of 10 mM MES pH 5.5, 30 μl of 1.0 M D-glucose, and 3 μl of carbohydrate oxidase.

gels were transblotted to PVDF membranes (Novex, San Diego, Calif.) for 2 hours at 25 volts in 10 mM CAPS pH 11.0 buffer. The PVDF membranes were stained in 0.1% Commassie Blue R250 in 40% methanol/1% acetic acid and the observed bands excised. The excised bands were sequenced from a blot cartridge using sequencing reagents (Perkin Elmer/Applied Biosystems Division, Foster City, Calif.). Detection of phenylthiohydantoin-amino acids was accomplished by on-line HPLC using Buffer A containing 3.5% tetrahydrofuran in water with 18 ml of the Premix concentrate (Perkin Elmer/Applied Biosystems Division, Foster City, Calif.) containing acetic acid, sodium acetate, and sodium hexanesulfonate and Buffer B containing acetonitrile. Data was collected and analyzed on a Macintosh IIsi using Applied Biosystems 610 Data Analysis software.

N-terminal sequencing of the both excised bands produced the sequence shown at positions 1–21 of SEQ ID NO: 2 where position 6 was not determinable but based on the deduced amino acid sequence is a cysteine. The N-terminus results agreed with the deduced amino acid sequence, and indicated a correct processing by both the *Aspergillus oryzae* and *Fusarium venenatum* hosts.

In 10 mM MES-NaCl pH 5.5, the recombinant carbohydrate oxidase had a UV-visible spectrum typical for flavoproteins as recorded on a Shimadzu UV160U spectrophotometer with 1-cm quartz cuvette. The relative absorbance at 280 and 450 nm was 19, slightly larger than the 12 value obtained for the wild-type enzyme. The extinction coefficient at 280 nm was measured by amino acid analysis to be 1.9 g/(l×cm), whereas the predicted value was 2.1 (including the contribution from a FAD molecule). Thus, it appeared that each recombinant carbohydrate oxidase contained one flavin molecule (likely FAD).

Assuming that the oxidation of each D-glucose molecule was coupled to the reduction of one $O_2$ to $H_2O_2$, recombinant carbohydrate oxidase activity was measured using a Hansatech $O_2$ electrode as described in Example 10. The Purification of the recombinant carbohydrate oxidase

|  | Vol | $A_{280}$ | $A_{280} \times V$ | $A_{450}$ | $A_{450} \times V$ | $A_{280}/A_{450}$ | Activity | Recovery |
|---|---|---|---|---|---|---|---|---|
| Broth | 2580 | 51.3 | 100 | 1.9 | 100 | 27 | 8.2 | 100 |
| Ultrafiltration | 512 | 44.2 | 17 | 2.35 | 25 | 19 | 45 | 107 |
| Q-Sepharose | 768 | 20.7 | 12 | 1 | 16 | 21 | 24 | 87 |
| SP-Sepharose | 144 | 52.6 | 5.7 | 3.7 | 11 | 19 | 45 | 31 |

Units: Vol, ml; A × V and Recovery (Activity × Vol), %; Activity (Peroxidase/o-anisidine assay), IU/ml.

Example 11

Molecular Properties of Recombinant Carbohydrate Oxidase

SDS-PAGE using a Novex 8–16% Tris-glycine SDS-PAGE gel indicated that the recombinant carbohydrate oxidases obtained as described in Examples 8 and 9 have a molecular weight of approximately 55 kDa, similar to the wild-type carbohydrate oxidase.

N-terminal sequencing of the recombinant carbohydrate oxidases was performed on an Applied Biosystems 476A Protein Sequencer (Perkin Elmer/Applied Biosystems Division, Foster City, Calif.) with on-line HPLC and liquid phase trifluoroacetic acid (TFA) delivery. The recombinant carbohydrate oxidases preparations were submitted to SDS-PAGE using Novex 10% Bis-Tris- SDS-PAGE gel using Novex Nupage MOPS buffer under reducing conditions. The recombinant carbohydrate oxidase oxidized D-glucose (0.1 M) at a specific activity of 4.0 IU/$A_{280}$ or 116 turnover/minute at pH 5.5 and 20° C. As assayed by the *Coprinus cinereus* peroxidase/anisidine method described in Example 8, the recombinant carbohydrate oxidase had the same specific activity as wild-type enzyme.

Example 12

Substrate Specificity

Substrate Specificity at 60 mM Substrate Concentration

The substrate specificity for the carbohydrate oxidase from *M. nivale* was determined in a microplate at ambient temperature by mixing in the following order:

50 μl 0.4/0.4 M phosphate/citrate buffer (pH 6)

50 μl substrate (360 mM)

50 μl 21.6 mM 3-Dimethylaminobenzoic acid (DMAB)

50 μl 1 mM 3-Methyl-2-benzothiazolinone hydrazone (MBTH)

50 μl 75 μg/ml, rec. *Coprinus cinereus* peroxidase (rCiP)

50 μl carbohydrate oxidase

The absorbance at 595 nm was followed for at least 3 minutes. The increase in absorbance per minute was calculated and used as a measure for relative activity.

The results of the oxidizing activity of the carbohydrate oxidase of the present invention on various mono- and disaccharide substrates are summarized in the table below and show that the carbohydrate oxidase can oxidize most reducing sugars and shows higher activity on maltose and cellobiose than the corresponding monosaccharide glucose. The enzyme had no activity on non-reducing sugars, such as fructose, sucrose, trehalose, and methyl-b-D-glucopyranoside. The results are shown as substrate specificity of *M. nivale* oxidase, relative to the optimum activity on D-cellobiose.

| Substrate | & Activity |
| --- | --- |
| D-Glucose | 69 |
| 2-Deoxy-D-Glucose | 4.2 |
| D-Galactose | 31.3 |
| D-Mannose | 3.2 |
| D-Xylose | 55.6 |
| D-Maltose | 83.5 |
| D-Cellobiose | "100" |
| Lactose | 52.5 |

Substrate Specificity at 0.83 mM

Further analyses of substrate specificity revealed that the carbohydrate oxidase from *M. nivale* is capable of oxidizing oligosaccharides of all degrees of polymerization (DP) which were tested, DP2-DP5, using the assay conditions described above, except to change the substrate concentration to 0.83 mM. Furthermore, the enzyme can hydrolyze both maltodextrins and cellodextrins wherein the monosaccharide units are linked by alpha-1,4 or beta-1,4 glucosidic bonds, respectively. The carbohydrate oxidase hydrolyzed all cellodextrins tested equally well and at a level around 10-fold higher than the monosaccharide. With maltodextrins as the substrate, the activity of the carbohydrate oxidase ranged from 1½-fold higher for maltohexaose to almost 5-fold higher for maltotetraose than for the monosaccharide. The results are summarized in the table below, showing the influence of the degree of polymerization and type of 1,4 linkage on carbohydrate oxidase activity relative to DP 1 (D-glucose).

| | % Activity | |
| --- | --- | --- |
| DP | alpha-1.4 | beta-1.4 |
| 1 | "100" | |
| 2 | 211 | 949 |
| 3 | 348 | 1147 |
| 4 | 477 | 1111 |
| 5 | 161 | 1014 |

Substrate Specificity at 1% Substrate Concentration

Analyses of the oxidizing activity of the carbohydrate oxidase from *M. nivale* on polysaccharides revealed that the enzyme is capable of significant activity on carboxymethylcellulose (CMC), even after removal of smaller oligosaccharides and monosaccharides by dialysis when tested under the assay conditions described above using a substrate concentration of 1%. The results are summarized in the table below which shows the carbohydrate oxidase activity on carboxymethylcellulose relative to D-cellobiose.

| Substrate | % Activity |
| --- | --- |
| D-cellobiose | "100" |
| CMC | 17.7 |
| CMC, dialyzed | 8.8 |

Substrate Specificity at 10 mM Substrate Concentration

The oxidizing activity of the carbohydrate oxidase from *M. nivale* on various substrates was measured at pH 7.8 (50 mM Tris-HCl buffer), 10 mM of substrate. Similar data for carbohydrate oxidase from Acremonium are included for comparison (as described in BBA (1991) 1118, 41–47).

| | Microdochium | Acremonium |
| --- | --- | --- |
| Maltose | 76.1 | 100 |
| Maltotriose | 84.9 | 94 |
| Maltotetraose | 100.0 | 74 |
| Maltopentaose | 58.6 | 46 |
| Maltohexaose | 41.2 | 66 |
| Maltoheptaose | 32.5 | 56 |
| Lactose | 67.0 | 59 |
| Glucose | 39.6 | 64 |
| Cellobiose | 65.7 | 47 |

Example 13

Oxidation of Maltose

To demonstrate that the reducing group at the 1-position is oxidized by the carbohydrate oxidase from *M. nivale*, the oxidation of maltose was followed chromatographically under the following conditions: 125 μl of 0.2 M citrate-phosphate buffer, pH 6 was added to 250 μl 10 mM maltose and 75 μl water before adding 50 μl purified *M. nivale* carbohydrate oxidase. The sample was incubated up to 30 minutes at 40° C. with constant shaking. The reaction was stopped by adding 100 μl of the sample to 900 μl water at 95° C. 50 μl of the reaction mix was then analyzed by anion exchange chromatography (CarboPac PA1 column, Dionex) followed by pulsed amperometric detection (Dionex) on the Dionex DX-500 system using the following conditions:

| | |
| --- | --- |
| Flow rate: | 1 ml/min |
| A-buffer: | 0.1 M NaOH (degassed in He) |
| B-buffer: | 0.1 M NaOH, 0.6 mM sodium acetate (degassed in He) |
| Gradient: | 0–3 min, 5% B–buffer |
| | 3–19 min, 5–30% B–buffer |
| | 19–21 min, 30–100% B–buffer |
| | 21–23 min, 100% B–buffer |
| | 23–24 min 100–5% B–buffer |

Standard maltodextrins (DP1-7) were purchased from Sigma Chemical Co. Maltobionic acid was prepared according to Fitting & Putman (1952) J. Biol. Chem. 199:573.

Using the above method, maltose is detected as a peak with a retention time around 8.0 minutes, while maltobionic acid is detected as a peak with a retention time around 13.3 minutes. At the above conditions, maltobionic acid is generated from maltose in the presence of the *M. nivale* carbohydrate oxidase, as a peak develops around 13.3 minutes.

Thus, the carbohydrate oxidase oxidizes the free reducing end group in maltose. The amount of maltobionic acid produced is presented below as $\mu$M maltobionic acid in reaction mixture:

| Incubation time (minutes) | Maltobionic acid ($\mu$M) |
|---|---|
| 0 | 0 |
| 5 | 150 |
| 10 | 370 |
| 30 | 880 |

Example 14
Binding Constant, $K_m$

Steady state kinetics was conducted by varying the concentration of the carbohydrate substrates and determining the carbohydrate oxidase activity by the 4AA-TOPS assay. Simple Michaelis-Menten kinetics was assumed although the reaction is not a simple one substrate-one product mechanism (E+S⇌ES→E+P).

The steady state kinetics for the carbohydrate oxidase from *M. nivale* were investigated using some of the preferred substrates. Kinetic constants were obtained from a Lineweaver-Burke plot, assuming simple Michaelis-Menten kinetics (although this is a rather poor assumption) to obtain apparent values "$K_m$" and "$V_{max}$" for various substrates. The results for "$K_m$" were:

| | |
|---|---|
| Glucose: | 42 mM |
| Maltose: | 11 mM |
| Cellobiose | 59 mM |

The carbohydrate oxidase shows the highest activity on cellobiose; however, "$K_m$" for cellobiose is almost 6 fold higher than for maltose. Likewise the "$K_m$" for glucose is significantly higher than for maltose, while the "$V_{max}$" is more or less the same for the two substrates. Thus, the previously shown preference for maltose at the low concentrations of substrate is explained by the lower value of "$K_m$" for maltose.

Example 15
pH and Temperature Activity Profiles

The activity of the carbohydrate oxidase from *M. nivale* over a pH range was determined in microplates at ambient temperature using the method described above in Example 12, but with buffers adjusted to the pH being tested; the actual pH was measured in the reaction mixture. The results below (activity relative to the optimum at pH 6.32) show that the carbohydrate oxidase has optimum activity at pH 5–7, and it has a reasonably broad pH activity profile.

| pH | % activity |
|---|---|
| 3.38 | 5.58 |
| 4.28 | 27.69 |
| 5.31 | 88.97 |
| 6.32 | 100.00 |
| 7.15 | 96.20 |
| 8.05 | 57.25 |

The temperature activity profile for the carbohydrate oxidase was determined by mixing buffer and substrate in a glass tube and preincubating at various temperatures (30–80° C.) for at least minutes:

150 ml 0.4/0.4 M phosphate/citrate pH 6
150 ml 180 mM maltose
150 ml oxidase dilution Reactions were started by addition of oxidase and samples were incubated at the appropriate temperature in a thermostatic bath, set at. After 5 minutes the samples were placed on ice, and formation of $H_2O_2$ was determined by addition of 450 $\mu$l of DMAB:MBTH:rCiP (1:1:1) at the respective concentrations as in Example 12 and the increase in absorbance at 590 nm was measured after 10 seconds on a HP 8452A diode array spectrophotometer (Hewlett-Packard). A blind without incubation was included. The results shown below (relative to the optimum at 50° C.) indicate that the enzyme is active up to at least 60° C. with an optimum activity at 50° C.

| ° C. | % activity |
|---|---|
| 30 | 86.28 |
| 40 | 90.98 |
| 50 | 100.00 |
| 60 | 79.95 |
| 70 | 2.27 |

Example 16
Thermostability by DSC

A sample of carbohydrate from *M. nivale* was desalted into 0.1 M MES, pH 6 using the NAP-5 columns from Pharmacia. The sample (contianing 6.5 mg/ml of the oxidase) was loaded onto the VP-DSC apparatus (MicroCal) and a linear scan from 20 to 90° C. was conducted at a scan rate of 90°/h.

The denaturation temperature was found to be 73° C.
Temperature and pH Stability
Temperature Stability The carbohydrate oxidase from *M. nivale* was preincubated 10 minutes at pH 6 at varying temperatures before measuring the residual activity by the 4AA-TOPS

| Temp ° C.: | Residual Activity %: |
|---|---|
| 40 | 81 |
| 50 | 78 |
| 60 | 100 |
| 70 | 19 |
| 80 | 2 |

The results shows that the enzyme is stable up to 60° C. but unstable at 70° C. and above. This is in accordance with result obtained from DSC experiments.
pH-stability The carbohydrate oxidase from *M. nivale* was incubated for 2 hours at 40° C. at varying pH before measuring the residual activity by the 4AA-TOPS assay:

| pH: | Res. Act. %: |
|---|---|
| 3 | 2 |
| 4 | 100 |
| 5 | 95 |

-continued

| pH: | Res. Act. %: |
|-----|--------------|
| 6   | 93           |
| 7   | 99           |
| 8   | 97           |
| 9   | 93           |

The results shows that the enzyme is stable in the range from pH 4–9 but unstable at pH 3.

Example 18
Effect of Carbohydrate Oxidase on Gluten Rheology

| Bread dough recipe | |
|---|---|
| Wheat Flour | 100% (= 10 g) |
| Water | 58% (including enzyme solution) |
| Salt | 1.5% |
| Sugar | 1.5% |

The wheat flour was of the type Meneba. The flour was free of ascorbic acid.

The dough was mixed in a 10 g Micro Mixer (type NSI-33R, from National Manufacturing Co.) for 2:30 minutes. Carbohydrate oxidase from *M. nivale* was added before mixing. After mixing, the dough was allowed to rest for 90 minutes at 32° C. and 85% relative humidity. Gluten was washed out of the dough with a solution of 2% NaCl (7 minutes in a Glutomatic 2200, Perten Instruments), and then centrifuged in a Gluten Index Centrifuge 2015 (Perten Instruments) for 1 minute.

Gluten rheology was analyzed in a Bohlin VOR rheometer system (Bohlin Instruments), performing a strain sweep at constant frequency (1 Hz), in order to evaluate the strength of the dough under oscillation. In this method, the viscoelastic properties of the dough are divided into two components, the dynamic shear storage modulus G' and the dynamic shear loss modulus G". The ratio of the loss and the storage moduli is numerically equal to the tangent of the viscoelastic phase angle d. An increase in the storage modulus G' and a decrease in the phase angle d indicate a stronger and more elastic dough.

| Carbohydrate Oxidase | G' | G" | d |
|---|---|---|---|
| None (Reference) | 349.5 | 166.4 | 25.46 |
| 50 U/kg flour | 397.9 | 176.3 | 23.89* |
| 100 U/kg flour | 456.3* | 193.7* | 23.02* |
| 200 U/kg flour | 523.0* | 207.4* | 21.77* |
| 500 U/kg flour | 554.7* | 207.3* | 20.49* |
| 1000 U/kg flour | 708.5* | 249.4* | 19.40* |

The results show that the G' storage modulus rises in proportion to the dose of carbohydrate oxidase added to the dough. With respect to the d phase angle, all the carbohydrate oxidase-treated doughs are different from the reference, and the phase angle decreases proportionally with the amount of enzyme added. Thus, the carbohydrate oxidase increases the elastic module, and hence increases dough elasticity, in a dose-dependent manner. The figures are the average of three independent measurements. Figures denoted with an asterisk are statistically significant from the reference by ANOVA analysis at a 5% level of significance.

Example 19
Effect of Carbohydrate Oxidase on Dough Consistency

| Baking Procedure | | |
|---|---|---|
| Basic recipe: | Flour (Meneba) | 12 g (°100%) |
| | Water | 60% (including enzyme solution) |
| | Yeast | 4% |
| | Sugar | 1.5% |
| | NaCl | 1.5% |

The flour was free of ascorbic acid.

Procedure: The dough was mixed in a 10 g Micro Mixer (type NSI-33R, from National Manufacturing Co.) for 2½ minutes. Carbohydrate oxidase from *M. nivale* was added before mixing. The final dough temperature after mixing was approx. 27° C. The dough was evaluated immediately after mixing.

Evaluation of Dough

Dough stickiness and firmness were measured empirically according to the following scale:

| Scoring system | 1 | 2 | 3 | 4 | 5 | 6 |
|---|---|---|---|---|---|---|
| Firmness: | very soft | too soft | soft/good | normal | firm | too firm |
| Stickiness: | almost liquid | too sticky | sticky | good | dry | too dry |

The evaluation was conducted over two days, using three replicates for each dose per day. The data, summarized in the table below, represent the mean value of six evaluations. The results indicate that both dough firmness and stickiness show the same tendency of a dose-dependent increase in the ability of the carbohydrate oxidase to yield a dough with excellent dough consistency. At 200 and 300 Units/kg, a skilled baker evaluated the dough as having an excellent firmness and softness, and a very airy consistency.

| Carbohydrate Oxidase | Firmness | Stickiness |
|---|---|---|
| None (Reference) | 3.0 | 2.3 |
| 10 U/kg flour | 3.0 | 3.0 |
| 50 U/kg flour | 3.5 | 3.4 |
| 100 U/kg flour | 4.0 | 4.0 |
| 200 U/kg flour | 4.0 | 3.8 |
| 300 U/kg flour | 4.1 | 4.1 |
| 500 U/kg flour | 4.8 | 4.8 |
| Bromate | 4.0 | 3.5 |

Example 20

In order to test the tolerance of *Microdochium nivale* carbohydrate oxidase (MCO) towards variations in different processing parameters, MCO has been tested in a "European straight dough", standard scale baking test (2 kg flour). Compared to the standard baking procedure (ABF-SP.1217.01/01), the dough was strained by increasing the water content, by increasing the mixing time, and/or by increasing the fermentation time. The trial aimed to clarify if MCO can make the dough more resistant to these changes. To simulate a realistic baking procedure MCO was tested in combination with Fungamyl Super MA (xylanase and amylase). The set-up was based on a non-complete statistical design. Compared to a control, not containing MCO, the addition of MCO resulted in better dough/bread robustness. E.g. when evaluating the standing (=area of "foot") it can e.g. be concluded that no significant interactions were observed between MCO dosage (0–200 U) and an increase of the water addition by 1.5% and increase of the mixing time by +2 min.

What is claimed is:

1. An isolated carbohydrate oxidase selected from the group consisting of:
   (a) a polypeptide encoded by the carbohydrate oxidase-encoding part of the DNA sequence cloned into a plasmid present in *Escherichia coli* NRRL B-30034, wherein the plasmid is pCR2.1-TOPO;
   (b) a polypeptide having an amino acid sequence as shown in SEQ ID NO: 2, or a fragment thereof exhibiting carbohydrate oxidase activity; and
   (c) a polypeptide having at least 90% identity to the polypeptide of (a)–(b) and exhibiting carbohydrate oxidase activity.

2. The isolated carbohydrate oxidase of claim 1, wherein the polypeptide is produced by *Microdochium nivale* CBS 100236.

3. The isolated carbohydrate oxidase of claim 1 selected from (a) or (b).

4. A dough-improving additive comprising:
   a) the carbohydrate oxidase of claim 1 which has has a higher activity on an oligosaccharide substrate having a degree of polymerization of 2 or higher relative to its activity on the corresponding monosaccharide; and
   b) a second enzyme selected from the group consisting of amylase, cellulose, hemicellulase, lipase and phospholipase.

5. The composition of claim 4 wherein the second enzyme is an amylase which hydrolyzes starch to form oligosaccharides as a main product.

6. The composition of claim 5 wherein the amylase is selected from the group consisting of a *Bacillus stearothermophilus* maltogenic alpha-amylase, an *Aspergillus oryzae* alpha-amylase, and a beta-amylase.

7. A dough-improving additive, which comprises the carbohydrate oxidase of claim 1 which has a higher activity on an oligosaccharide substrate having a degree of polymerization of 2 or higher relative to its activity on the corresponding monosaccharide, wherein said additive is in the form of a granulate or agglomerated powder.

8. The additive of claim 7 wherein more than 95% of said additive has a particle size between 25 and 500 μm.

9. The carbohydrate oxidase of claim 1, wherein said carbohydrate oxidase is produced by *Microdochium nivale.*

10. A method for producing the carbohydrate oxidase of claim 1, said method comprising (i) cultivating a carbohydrate oxidase producing strain of Microdochium in a suitable nutrient medium, and (ii) recovering the carbohydrate oxidase.

11. The method claim 10, wherein said strain is a strain of *M. nivale.*

12. A carbohydrate oxidase which is derived from a strain of Microdochium and has an oxidizing activity on maltotetraose as a substrate which is at least twice as much as its oxidizing activity on glucose as a substrate, when said activities are measured at a substrate concentration of 0.83 mM.

13. The carbohydrate oxidase of claim 12 which is derived from a strain of *M. nivale.*

* * * * *

```
                              SEQUENCE LISTING

<160> NUMBER OF SEQ ID NOS: 23

<210> SEQ ID NO 1
<211> LENGTH: 1553
<212> TYPE: DNA
<213> ORGANISM: Microdochium nivale
<220> FEATURE:
<221> NAME/KEY: intron
<222> LOCATION: (1012)..(1076)
<220> FEATURE:
<221> NAME/KEY: CDS
<222> LOCATION: (1)..(1011)
<220> FEATURE:
<221> NAME/KEY: CDS
<222> LOCATION: (1077)..(1553)
<220> FEATURE:
<221> NAME/KEY: mat_peptide
<222> LOCATION: (67)..(1550)

<400> SEQUENCE: 1 atg cgt tct gca ttt atc ttg gcc ctc ggc ctt atc acc gcc agc gct         48
Met Arg Ser Ala Phe Ile Leu Ala Leu Gly Leu Ile Thr Ala Ser Ala
        -20             -15                 -10 gac gct tta gtc act cgc ggt gcc atc gag gcc tgc ctg tct gct gct         96
Asp Ala Leu Val Thr Arg Gly Ala Ile Glu Ala Cys Leu Ser Ala Ala
    -5              -1   1               5                  10 ggc gtc ccg atc gat att cct ggc act gcc gac tat gag cgc gat gtc        144
Gly Val Pro Ile Asp Ile Pro Gly Thr Ala Asp Tyr Glu Arg Asp Val
                15                  20                  25 gag ccc ttc aac atc cgc ctg cca tac att ccc acc gcc att gct cag        192
Glu Pro Phe Asn Ile Arg Leu Pro Tyr Ile Pro Thr Ala Ile Ala Gln
                30                  35                  40 acg cag act act gct cac atc cag tcg gca gtc cag tgc gcc aag aag        240
Thr Gln Thr Thr Ala His Ile Gln Ser Ala Val Gln Cys Ala Lys Lys
        45                  50                  55 ctc aac ctc aag gtc tct gcc aag tct ggt ggt cac agc tac gcc tcg        288
Leu Asn Leu Lys Val Ser Ala Lys Ser Gly Gly His Ser Tyr Ala Ser
    60                  65                  70 ttc ggc ttt ggt ggc gag aac ggt cac ctc atg gtc cag ctc gac cgc        336
Phe Gly Phe Gly Gly Glu Asn Gly His Leu Met Val Gln Leu Asp Arg
75                  80                  85                  90 atg att gat gtc atc tcg tac aat gac aag act ggc att gcc cat gtt        384
Met Ile Asp Val Ile Ser Tyr Asn Asp Lys Thr Gly Ile Ala His Val
                95                 100                 105 gag ccc ggt gcc cgc ctc gga cat ctc gcc acc gtc ctc aac gac aag        432
Glu Pro Gly Ala Arg Leu Gly His Leu Ala Thr Val Leu Asn Asp Lys
            110                 115                 120 tac ggc cgt gcc atc tcc cac ggt aca tgc cct ggt gtc ggc atc tcc        480
Tyr Gly Arg Ala Ile Ser His Gly Thr Cys Pro Gly Val Gly Ile Ser
        125                 130                 135 ggc cac ttt gcc cac ggc ggc ttc ggc ttc agc tcg cac atg cac ggt        528
Gly His Phe Ala His Gly Gly Phe Gly Phe Ser Ser His Met His Gly
    140                 145                 150 ctg gct gtc gac tcg gtc gtc ggt gtc act gtt gtt ctt gct gat gga        576
Leu Ala Val Asp Ser Val Val Gly Val Thr Val Val Leu Ala Asp Gly
155                 160                 165                 170
```

```
cgc atc gtt gag gct tct gcc act gag aat gct gac ctc ttc tgg ggt         624
Arg Ile Val Glu Ala Ser Ala Thr Glu Asn Ala Asp Leu Phe Trp Gly
            175                 180                 185 atc aag ggc gct ggc tcc aac ttc ggc atc gtt gct gtc tgg aag ctc         672
Ile Lys Gly Ala Gly Ser Asn Phe Gly Ile Val Ala Val Trp Lys Leu
        190                 195                 200 gcc act ttc cct gct ccc aag gtt ctc acc cgc ttt ggc gtc acc ctc         720
Ala Thr Phe Pro Ala Pro Lys Val Leu Thr Arg Phe Gly Val Thr Leu
        205                 210                 215 aac tgg aag aac aag acc tct gcc ctc aag ggc atc gag gct gtt gag         768
Asn Trp Lys Asn Lys Thr Ser Ala Leu Lys Gly Ile Glu Ala Val Glu
    220                 225                 230 gac tac gcc cgc tgg gtc gcc ccc cgc gag gtc aac ttc cgc att gga         816
Asp Tyr Ala Arg Trp Val Ala Pro Arg Glu Val Asn Phe Arg Ile Gly
235                 240                 245                 250 gac tac ggc gct ggt aac ccg ggt atc gag ggt ctc tac tac ggc act         864
Asp Tyr Gly Ala Gly Asn Pro Gly Ile Glu Gly Leu Tyr Tyr Gly Thr
                255                 260                 265 ccc gag caa tgg cgt gcg gct ttc caa cct ctg ctc gac act ctg cct         912
Pro Glu Gln Trp Arg Ala Ala Phe Gln Pro Leu Leu Asp Thr Leu Pro
            270                 275                 280 gct gga tac gtt gtc aac ccg acc acc tcc ttg aac tgg atc gag tcg         960
Ala Gly Tyr Val Val Asn Pro Thr Thr Ser Leu Asn Trp Ile Glu Ser
        285                 290                 295 gtg ctc agc tac tcc aac ttt gac cat gtc gac ttc att act cct cag        1008
Val Leu Ser Tyr Ser Asn Phe Asp His Val Asp Phe Ile Thr Pro Gln
300                 305                 310 cct gtaagtgttc accgactttg cgctgggaga atgttttatg tcggctttac             1061
Pro
315 tgactccctc tacag gtc gag aac ttc tat gcc aag agc ttg acg ctc aag       1112
                 Val Glu Asn Phe Tyr Ala Lys Ser Leu Thr Leu Lys
                                         320                 325 agt atc aag ggc gac gcc gtc aag aac ttt gtc gac tac tac ttt gac        1160
Ser Ile Lys Gly Asp Ala Val Lys Asn Phe Val Asp Tyr Tyr Phe Asp
        330                 335                 340 gtg tcc aac aag gtt aag gac cgc ttc tgg ttc tac cag ctc gac gtg        1208
Val Ser Asn Lys Val Lys Asp Arg Phe Trp Phe Tyr Gln Leu Asp Val
    345                 350                 355 cac ggc ggc aag aac tcg caa gtc acc aag gtc acc aac gcc gag aca        1256
His Gly Gly Lys Asn Ser Gln Val Thr Lys Val Thr Asn Ala Glu Thr
360                 365                 370                 375 gcc tac cct cac cgc gac aag ctc tgg ctg atc cag ttc tac gac cgc        1304
Ala Tyr Pro His Arg Asp Lys Leu Trp Leu Ile Gln Phe Tyr Asp Arg
                380                 385                 390 tac gac aac aac cag acc tac ccg gag acc tca ttc aag ttc ctc gac        1352
Tyr Asp Asn Asn Gln Thr Tyr Pro Glu Thr Ser Phe Lys Phe Leu Asp
            395                 400                 405 ggc tgg gtc aac tcg gtc acc aag gct ctc ccc aag tcc gac tgg ggc        1400
Gly Trp Val Asn Ser Val Thr Lys Ala Leu Pro Lys Ser Asp Trp Gly
        410                 415                 420 atg tac atc aac tac gcc gac ccc cgc atg gac cgc gac tac gcc acc        1448
Met Tyr Ile Asn Tyr Ala Asp Pro Arg Met Asp Arg Asp Tyr Ala Thr
    425                 430                 435 aag gtc tac tac ggt gag aac ctc gcc agg ctc cag aag ctc aag gcc        1496
Lys Val Tyr Tyr Gly Glu Asn Leu Ala Arg Leu Gln Lys Leu Lys Ala
440                 445                 450                 455 aag ttt gat ccc acc gac cgt ttc tac tac cct cag gct gtc cgc cct        1544
Lys Phe Asp Pro Thr Asp Arg Phe Tyr Tyr Pro Gln Ala Val Arg Pro
                460                 465                 470
```

```
gtc aaa taa                                                         1553
Val Lys <210> SEQ ID NO 2
<211> LENGTH: 495
<212> TYPE: PRT
<213> ORGANISM: Microdochium nivale

<400> SEQUENCE: 2

Met Arg Ser Ala Phe Ile Leu Ala Leu Gly Leu Ile Thr Ala Ser Ala
 1               5                  10                  15

Asp Ala Leu Val Thr Arg Gly Ala Ile Glu Ala Cys Leu Ser Ala Ala
            20                  25                  30

Gly Val Pro Ile Asp Ile Pro Gly Thr Ala Asp Tyr Glu Arg Asp Val
        35                  40                  45

Glu Pro Phe Asn Ile Arg Leu Pro Tyr Ile Pro Thr Ala Ile Ala Gln
    50                  55                  60

Thr Gln Thr Thr Ala His Ile Gln Ser Ala Val Gln Cys Ala Lys Lys
65                  70                  75                  80

Leu Asn Leu Lys Val Ser Ala Lys Ser Gly Gly His Ser Tyr Ala Ser
                85                  90                  95

Phe Gly Phe Gly Gly Glu Asn Gly His Leu Met Val Gln Leu Asp Arg
            100                 105                 110

Met Ile Asp Val Ile Ser Tyr Asn Asp Lys Thr Gly Ile Ala His Val
        115                 120                 125

Glu Pro Gly Ala Arg Leu Gly His Leu Ala Thr Val Leu Asn Asp Lys
    130                 135                 140

Tyr Gly Arg Ala Ile Ser His Gly Thr Cys Pro Gly Val Gly Ile Ser
145                 150                 155                 160

Gly His Phe Ala His Gly Gly Phe Gly Phe Ser Ser His Met His Gly
                165                 170                 175

Leu Ala Val Asp Ser Val Val Gly Val Thr Val Leu Ala Asp Gly
            180                 185                 190

Arg Ile Val Glu Ala Ser Ala Thr Glu Asn Ala Asp Leu Phe Trp Gly
    195                 200                 205

Ile Lys Gly Ala Gly Ser Asn Phe Gly Ile Val Ala Val Trp Lys Leu
210                 215                 220

Ala Thr Phe Pro Ala Pro Lys Val Leu Thr Arg Phe Gly Val Thr Leu
225                 230                 235                 240

Asn Trp Lys Asn Lys Thr Ser Ala Leu Lys Gly Ile Glu Ala Val Glu
                245                 250                 255

Asp Tyr Ala Arg Trp Val Ala Pro Arg Glu Val Asn Phe Arg Ile Gly
            260                 265                 270

Asp Tyr Gly Ala Gly Asn Pro Gly Ile Glu Gly Leu Tyr Tyr Gly Thr
        275                 280                 285

Pro Glu Gln Trp Arg Ala Ala Phe Gln Pro Leu Leu Asp Thr Leu Pro
    290                 295                 300

Ala Gly Tyr Val Val Asn Pro Thr Thr Ser Leu Asn Trp Ile Glu Ser
305                 310                 315                 320

Val Leu Ser Tyr Ser Asn Phe Asp His Val Asp Phe Ile Thr Pro Gln
                325                 330                 335

Pro Val Glu Asn Phe Tyr Ala Lys Ser Leu Thr Leu Lys Ser Ile Lys
            340                 345                 350
```

```
Gly Asp Ala Val Lys Asn Phe Val Asp Tyr Tyr Phe Asp Val Ser Asn
            355                 360                 365

Lys Val Lys Asp Arg Phe Trp Phe Tyr Gln Leu Asp Val His Gly Gly
370                 375                 380

Lys Asn Ser Gln Val Thr Lys Val Thr Asn Ala Glu Thr Ala Tyr Pro
385                 390                 395                 400

His Arg Asp Lys Leu Trp Leu Ile Gln Phe Tyr Asp Arg Tyr Asp Asn
                405                 410                 415

Asn Gln Thr Tyr Pro Glu Thr Ser Phe Lys Phe Leu Asp Gly Trp Val
            420                 425                 430

Asn Ser Val Thr Lys Ala Leu Pro Lys Ser Asp Trp Gly Met Tyr Ile
            435                 440                 445

Asn Tyr Ala Asp Pro Arg Met Asp Arg Asp Tyr Ala Thr Lys Val Tyr
450                 455                 460

Tyr Gly Glu Asn Leu Ala Arg Leu Gln Lys Leu Lys Ala Lys Phe Asp
465                 470                 475                 480

Pro Thr Asp Arg Phe Tyr Tyr Pro Gln Ala Val Arg Pro Val Lys
                485                 490                 495

<210> SEQ ID NO 3
<211> LENGTH: 23
<212> TYPE: DNA
<213> ORGANISM: Artificial Sequence
<220> FEATURE:
<223> OTHER INFORMATION: Primer
<220> FEATURE:
<223> OTHER INFORMATION: Primer
<220> FEATURE:
<221> NAME/KEY: modified_base
<222> LOCATION: (3)
<223> OTHER INFORMATION: i
<220> FEATURE:
<221> NAME/KEY: modified_base
<222> LOCATION: (6)
<223> OTHER INFORMATION: i
<220> FEATURE:
<221> NAME/KEY: modified_base
<222> LOCATION: (9)
<223> OTHER INFORMATION: i
<220> FEATURE:
<221> NAME/KEY: modified_base
<222> LOCATION: (12)
<223> OTHER INFORMATION: i
<220> FEATURE:
<221> NAME/KEY: modified_base
<222> LOCATION: (15)
<223> OTHER INFORMATION: i

<400> SEQUENCE: 3
gcngcnggng tnccnathga yat                                        23

<210> SEQ ID NO 4
<211> LENGTH: 24
<212> TYPE: DNA
<213> ORGANISM: Artificial Sequence
<220> FEATURE:
<223> OTHER INFORMATION: Primer
<220> FEATURE:
<221> NAME/KEY: modified_base
<222> LOCATION: (1)
<223> OTHER INFORMATION: i
<220> FEATURE:
<221> NAME/KEY: modified_base
<222> LOCATION: (7)
<223> OTHER INFORMATION: i
```

-continued

```
<400> SEQUENCE: 4
nggrtcngcr tarttdatrt acat                                      24

<210> SEQ ID NO 5
<211> LENGTH: 21
<212> TYPE: DNA
<213> ORGANISM: Artificial Sequence
<220> FEATURE:
<223> OTHER INFORMATION: Primer

<400> SEQUENCE: 5
tccagttcta cgaccgctac g                                         21

<210> SEQ ID NO 6
<211> LENGTH: 21
<212> TYPE: DNA
<213> ORGANISM: Artificial Sequence
<220> FEATURE:
<223> OTHER INFORMATION: Primer

<400> SEQUENCE: 6
cagacttggc agagaccttg a                                         21

<210> SEQ ID NO 7
<211> LENGTH: 27
<212> TYPE: DNA
<213> ORGANISM: Artificial Sequence
<220> FEATURE:
<223> OTHER INFORMATION: Primer
<220> FEATURE:
<221> NAME/KEY: modified_base
<222> LOCATION: (1)
OTHER INFORMATION:       i
<220> FEATURE:
<221> NAME/KEY: modified_base
<222> LOCATION: (19)
<223> OTHER INFORMATION: i

<400> SEQUENCE: 7
nacrtcraar tartartcna craartt                                   27

<210> SEQ ID NO 8
<211> LENGTH: 15
<212> TYPE: DNA
<213> ORGANISM: Artificial Sequence
<220> FEATURE:
<223> OTHER INFORMATION: Primer
<220> FEATURE:
<221> NAME/KEY: modified_base
<222> LOCATION: (4)
<223> OTHER INFORMATION: i
<220> FEATURE:
<221> NAME/KEY: modified_base
<222> LOCATION: (10)
<223> OTHER INFORMATION: i

<400> SEQUENCE: 8
rttnacccan ccrtc                                                15

<210> SEQ ID NO 9
<211> LENGTH: 24
<212> TYPE: DNA
<213> ORGANISM: Artificial Sequence
<220> FEATURE:
<223> OTHER INFORMATION: Primer

<400> SEQUENCE: 9
nggrtcngcr tarttdatrt acat                                      24
```

-continued

```
<210> SEQ ID NO 10
<211> LENGTH: 24
<212> TYPE: DNA
<213> ORGANISM: Artificial Sequence
<220> FEATURE:
<223> OTHER INFORMATION: Primer

<400> SEQUENCE: 10
datraartcn acrtgrtcra artt                                              24

<210> SEQ ID NO 11
<211> LENGTH: 24
<212> TYPE: DNA
<213> ORGANISM: Artificial Sequence
<220> FEATURE:
<223> OTHER INFORMATION: Primer

<400> SEQUENCE: 11
ccaytgytcn ggngtnccrt arta                                              24

<210> SEQ ID NO 12
<211> LENGTH: 21
<212> TYPE: DNA
<213> ORGANISM: Artificial Sequence
<220> FEATURE:
<223> OTHER INFORMATION: Primer

<400> SEQUENCE: 12
ctcgccactt tccctgctcc c                                                 21

<210> SEQ ID NO 13
<211> LENGTH: 21
<212> TYPE: DNA
<213> ORGANISM: Artificial Sequence
<220> FEATURE:
<223> OTHER INFORMATION: Primer

<400> SEQUENCE: 13
ctcggtcacc aaggctctcc c                                                 21

<210> SEQ ID NO 14
<211> LENGTH: 21
<212> TYPE: DNA
<213> ORGANISM: Artificial Sequence
<220> FEATURE:
<223> OTHER INFORMATION: Primer

<400> SEQUENCE: 14
gaccgctacg acaacaacca g                                                 21

<210> SEQ ID NO 15
<211> LENGTH: 21
<212> TYPE: DNA
<213> ORGANISM: Artificial Sequence
<220> FEATURE:
<223> OTHER INFORMATION: Primer

<400> SEQUENCE: 15
tcggagaaat gagagcaacc a                                                 21

<210> SEQ ID NO 16
<211> LENGTH: 21
<212> TYPE: DNA
<213> ORGANISM: Artificial Sequence
<220> FEATURE:
```

<223> OTHER INFORMATION: Primer

<400> SEQUENCE: 16
agccgacgtc cagcatagca g                                    21

<210> SEQ ID NO 17
<211> LENGTH: 21
<212> TYPE: DNA
<213> ORGANISM: Artificial Sequence
<220> FEATURE:
<223> OTHER INFORMATION: Primer

<400> SEQUENCE: 17
accctaccat acgagttcac g                                    21

<210> SEQ ID NO 18
<211> LENGTH: 21
<212> TYPE: DNA
<213> ORGANISM: Artificial Sequence
<220> FEATURE:
<223> OTHER INFORMATION: Primer

<400> SEQUENCE: 18
ggtcgaatcg tcacaaagta t                                    21

<210> SEQ ID NO 19
<211> LENGTH: 21
<212> TYPE: DNA
<213> ORGANISM: Artificial Sequence
<220> FEATURE:
<223> OTHER INFORMATION: Primer

<400> SEQUENCE: 19
cactggactg ccgactggat g                                    21

<210> SEQ ID NO 20
<211> LENGTH: 18
<212> TYPE: DNA
<213> ORGANISM: Artificial Sequence
<220> FEATURE:
<223> OTHER INFORMATION: Primer

<400> SEQUENCE: 20
caacaaccag acctaccc                                        18

<210> SEQ ID NO 21
<211> LENGTH: 21
<212> TYPE: DNA
<213> ORGANISM: Artificial Sequence
<220> FEATURE:
<223> OTHER INFORMATION: Primer

<400> SEQUENCE: 21
ctcagcagca cttctttca t                                     21

<210> SEQ ID NO 22
<211> LENGTH: 30
<212> TYPE: DNA
<213> ORGANISM: Artificial Sequence
<220> FEATURE:
<223> OTHER INFORMATION: Primer

<400> SEQUENCE: 22
gatttaaata tgcgttctgc atttatcttg                           30

-continued

```
<210> SEQ ID NO 23
<211> LENGTH: 30
<212> TYPE: DNA
<213> ORGANISM: Artificial Sequence
<220> FEATURE:
<223> OTHER INFORMATION: Primer

<400> SEQUENCE: 23
gttaattaat tatttgacag ggcggacagc                                    30
```